United States Patent [19]

Desobry et al.

[11] Patent Number: 5,077,402

[45] Date of Patent: Dec. 31, 1991

[54] NOVEL ALPHA-AMINOACETOPHENONES AS PHOTOINITIATORS

[75] Inventors: Vincent Desobry, Marly; Kurt Dietliker, Fribourg; Rinaldo Hüsler, Marly; Werner Rutsch, Fribourg; Manfred Rembold, Aesch; Franciszek Sitek, Therwil, all of Switzerland

[73] Assignee: Ciba-Geigy Corporation, Ardsley, N.Y.

[21] Appl. No.: 501,409

[22] Filed: Mar. 28, 1990

Related U.S. Application Data

[63] Continuation of Ser. No. 403,004, Sep. 5, 1989, abandoned, which is a continuation of Ser. No. 172,618, Mar. 24, 1988, abandoned.

[30] Foreign Application Priority Data

Mar. 26, 1987 [CH] Switzerland .................. 1152/87

[51] Int. Cl.$^5$ .................. C08F 2/50; C07C 225/10; C07D 295/10
[52] U.S. Cl. .................. 544/87; 522/34; 522/36; 522/39; 522/96; 522/81; 522/107; 522/109; 522/121; 544/163; 544/171; 544/175; 544/130; 544/141; 544/121; 544/137; 558/405; 560/38; 564/342
[58] Field of Search .................. 522/34,39,36; 544/87,175,121,130,137,141,163,171; 558/405; 560/38; 564/342

[56] References Cited

U.S. PATENT DOCUMENTS

| | | | |
|---|---|---|---|
| 3,804,736 | 4/1974 | Pasternack et al. | 522/100 |
| 4,318,791 | 3/1982 | Felder et al. | 430/281 |
| 4,559,371 | 12/1985 | Hüsler et al. | 204/158 R |
| 4,582,862 | 4/1986 | Berner et al. | 522/14 |

FOREIGN PATENT DOCUMENTS 138754 4/1985 European Pat. Off. .

Primary Examiner—Marion E. Mc Camish
Assistant Examiner—Arthur H. Koeckert
Attorney, Agent, or Firm—Luther A. R. Hall

[57] ABSTRACT

Compounds of the formula I, II, III and IIIa

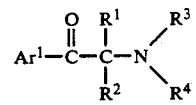

I

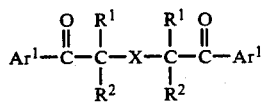

II

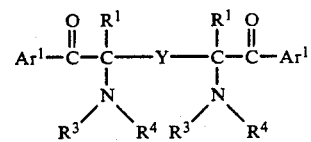

III

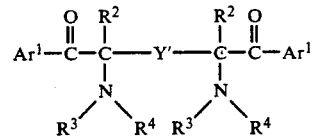

IIIa in which $Ar^1$ is an unsubstituted or substituted aromatic radical and at least one of the radicals $R^1$ and $R^2$ is an alkenyl, cycloalkenyl or arylmethyl group, are effective photoinitiators for photopolymerization of unsaturated compounds. They are particularly suitable for photocuring of pigmented systems.

8 Claims, No Drawings

NOVEL ALPHA-AMINOACETOPHENONES AS PHOTOINITIATORS

This application is a continuation of application Ser. No. 403,004, filed Sept 5, 1989, which is a continuation of Ser No. 172,618, filed Mar. 24, 1988, both now abandoned.

The invention relates to novel derivatives of α-aminoacetophenone which have an allyl or aralkyl group in the α-position, and to their use as photoinitiators for the photopolymerization of ethylenically unsaturated compounds, in particular for photocuring pigmented systems, such as printing inks or white lacquer.

Derivatives of α-aminoacetophenone are known from EP-A-3,002 as photoinitiators for ethylenically unsaturated compounds. If these compounds have in their 4-position of the phenyl radical substituents containing sulfur or oxygen, the compounds are particularly suitable as photoinitiators for pigmented photocurable systems (EP-A-88,050 and 117,233), for example for UV-curable printing inks.

Derivatives of α-aminoacetophenone which have an amino group in the 4-position of the phenyl radical are described in EP-A-138,754. These compounds are used in combination with photosensitizers from the aromatic carbonyl compound class.

It has now been found that of this general class of α-aminoacetophenones, those which contain at least one alkenyl or aralkyl group in the α-position have a particularly high activity as photoinitiators. These compounds are especially suitable for use in printing inks.

The compounds are specifically those of the formula I, II, III or IIIa,

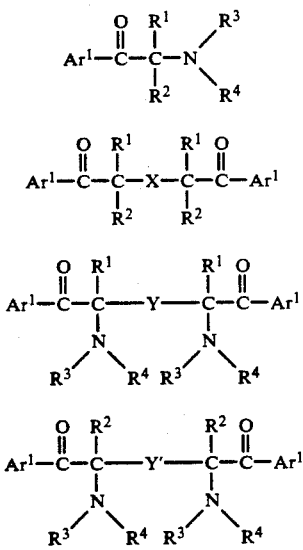

in which $Ar^1$ is an aromatic radical of the formula IV, V, VI or VII,

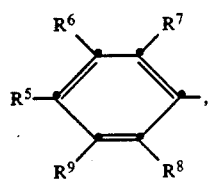

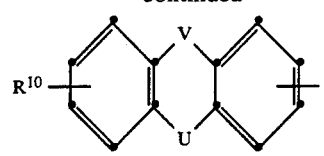

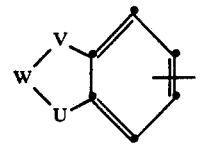

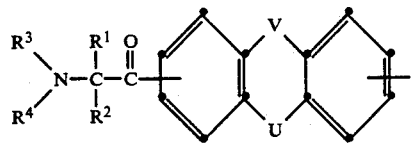

in which X is a divalent radical of the formula

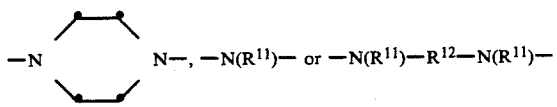

Y is $C_1$-$C_6$alkylene, cyclohexylene or a direct bond, Y' is xylylene, $C_4$-$C_8$alkenediyl, $C_6$-$C_{10}$alkadienediyl, dipentenediyl or dihydroxylylene, U is —O—, —S— or —N($R^{17}$)—, V is —O—, —S—, —N($R^{17}$)—, —CO—, —CH$_2$—, —CH$_2$CH$_2$—, $C_2$-$C_6$alkylidene or a direct bond, W is unbranched or branched $C_1$-$C_7$alkylene or $C_2$-$C_6$alkylidene, $R^1$ is either (a) a radical of the formula

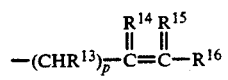

in which p is zero or 1, or (b) a radical of the formula

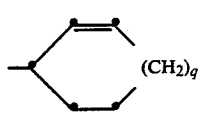

in which q is 0, 1, 2 or 3, or (c) a radical of the formula

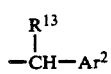

in which $Ar^2$ is a phenyl, naphthyl, furyl, thienyl or pyridyl radical which is unsubstituted or substituted by halogen, OH, $C_1$-$C_{12}$alkyl, $C_1$-$C_4$alkyl which is substituted by OH, halogen, —N($R^{11}$)$_2$, —$C_1$-$C_{12}$alkoxy, —COO($C_1$-$C_{18}$alkyl), —CO(OCH$_2$CH$_2$)$_n$OCH$_3$ or —OCO($C_1$-$C_4$)alkyl, $C_1$-$C_{12}$alkoxy, $C_1$-$C_4$alkoxy which is substituted by —COO($C_1$-$C_{18}$-alkyl) or —CO-(OCH$_2$CH$_2$)$_n$OCH$_3$, —(OCH$_2$CH$_2$)$_n$OH, —(OCH$_2$CH$_2$)$_n$OCH$_3$, $C_1$-$C_8$alkylthio, phenoxy, —COO($C_1$-$C_{18}$alkyl), —CO(OCH$_2$CH$_2$)$_n$OCH$_3$, phenyl or benzoyl, in which n is 1-20, or (d) together with $R^2$ forms a radical of the formula

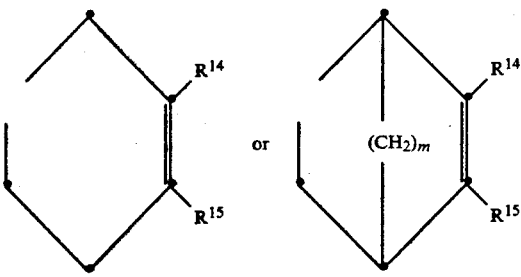

in which m is 1 or 2, $R^2$ has one of the meanings given for $R^1$ or is $C_5$–$C_6$ cycloalkyl, $C_1$–$C_{12}$alkyl which is unsubstituted or substituted by $C_1$–$C_4$alkoxy, phenoxy, halogen or phenyl, or phenyl which is unsubstituted or substituted by halogen, $C_1$–$C_{12}$alkyl or $C_1$–$C_4$alkoxy, $R^3$ is hydrogen, $C_1$–$C_{12}$alkyl, $C_2$–$C_4$alkyl which is substituted by hydroxyl, $C_1$–$C_4$alkoxy, —CN or —COO($C_1$–$C_4$alkyl), $C_3$–$C_5$alkenyl, $C_5$–$C_{12}$cycloalkyl or $C_7$–$C_9$phenylalkyl, $R^4$ is $C_1$–$C_{12}$alkyl, $C_2$–$C_4$alkyl which is substituted by hydroxyl, $C_1$–$C_4$alkoxy, —CN or —COO($C_1$–$C_4$alkyl), $C_3$–$C_5$-alkenyl, $C_5$–$C_{12}$cycloalkyl, $C_7$–$C_9$phenylalkyl, phenyl or phenyl which is substituted by halogen, $C_1$–$C_{12}$alkyl, $C_1$–$C_4$alkoxy or —COO($C_1$–$C_4$-alkyl or $R^4$ together with $R^2$ is $C_1$–$C_7$alkylene, $C_7$–$C_{10}$phenylalkylene, o-xylylene, 2-butenylene or $C_2$–$C_3$oxa- or -azaalkylene, or $R^3$ and $R^4$ together are $C_3$—$C_7$alkylene, which can be interrupted by —O—, —S—, —CO— or —N($R^{17}$)- or can be substituted by hydroxyl, $C_1$–$C_4$alkoxy or —COO($C_1$–$C_4$alkyl), $R^5$, $R^6$, $R^7$, $R^8$ and $R^9$ independently of one another are hydrogen, halogen, $C_1$–$C_{12}$alkyl, $C_5$–$C_6$cycloalkyl, phenyl, benzyl, benzoyl or a group —$OR^{18}$, —$SR^{19}$, —SO—$R^{19}$, —$SO_2$-$R^{19}$, —$N(R^{20})(R^{21})$, —NH—$SO_2$—$R^{22}$ or

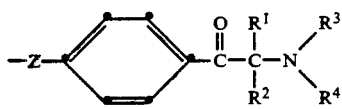

in which Z is —O—, —S—, —$N(R^{11})$—, —$N(R^1{}^1)$—$R^{12}$—$N(R^{11})$— or

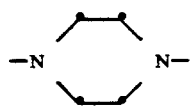

in which, in the case where $R^1$ is allyl and $R^2$ is methyl, $R^5$ is not —$OCH_3$, and in the case where $R^1$ is benzyl and $R^2$ is methyl or benzyl, $R^5$ is not —$OCH_3$, —$SCH_3$ or —SO—$CH_3$, $R^{10}$ is hydrogen, $C_1$–$C_{12}$alkyl, halogen or $C_2$–$C_8$alkanoyl, $R^{11}$ is hydrogen, $C_1$–$C_8$alkyl, $C_3$–$C_5$alkenyl, $C_7$–$C_9$phenylalkyl, $C_1$–$C_4$hydroxyalkyl or phenyl, $R^{12}$ is unbranched or branched $C_2$–$C_{16}$alkylene, which can be interrupted by one or more —O—, —S— or —$N(R^{11})$—, $R^{13}$ is hydrogen, $C_1$–$C_8$alkyl or phenyl, $R^{14}$, $R^{15}$ and $R^{16}$ independently of one another are hydrogen or $C_1$–$C_4$-alkyl, or $R^{14}$ and $R^{15}$ together are $C_3$–$C_7$alkylene, $R^{17}$ is hydrogen, $C_1$–$C_{12}$alkyl, which can be interrupted by one or more —O—, $C_3$–$C_5$-alkenyl, $C_7$–$C_9$phenylalkyl, $C_1$–$C_4$hydroxyalkyl, —$CH_2CH_2CN$, —$CH_2CH_2COO(C_1$–$C_4$alkyl), $C_2$–$C_8$alkanoyl or benzoyl, $R^{18}$ is hydrogen, $C_1$–$C_{12}$alkyl, $C_1$–$C_6$alkyl which is substituted by —CN, —OH, $C_1$–$C_4$alkoxy, $C_3$–$C_6$alkenoxy, —$OCH_2CH_2CN$, —$OCH_2CH_2COO(C_1$–$C_4$alkyl), —COOH or —COO($C_1$–$C_4$alkyl), —$(CH_2CH_2O)_nH$ where $n=2$–$20$, $C_2$–$C_8$alkanoyl, $C_3$–$C_{12}$alkenyl, cyclohexyl, hydroxycyclohexyl, phenyl, phenyl which is substituted by halogen, $C_1$–$C_{12}$alkyl or $C_1$–$C_4$alkoxy, $C_7$–$C_9$phenylalkyl or —$Si(C_1$–$C_8$alkyl)$_r$(phenyl)$_{3-r}$ where $r=1$, 2 or 3, $R^{19}$ is hydrogen, $C_1$–$C_{12}$alkyl, $C_3$–$C_{12}$alkenyl, cyclohexyl, $C_1$–$C_6$alkyl which is substituted by —SH, —OH, —CN, —COO($C_1$–$C_4$alkyl), $C_1$–$C_4$alkoxy, —$OCH_2CH_2CN$ or —$OCH_2CH_2COO(C_1$–$C_4$alkyl), phenyl, phenyl which is substituted by halogen, $C_1$–$C_{12}$alkyl or $C_1$–$C_4$alkoxy or $C_7$–$C_9$phenylalkyl, $R^{20}$ and $R^{21}$ independently of one another are hydrogen, $C_1$–$C_{12}$alkyl, $C_2$–$C_4$hydroxyalkyl, $C_2$–$C_{10}$alkoxyalkyl, $C_3$–$C_5$alkenyl, $C_5$–$C_{12}$cycloalkyl, $C_7$–$C_9$phenylalkyl, phenyl, phenyl which is substituted by halogen, $C_1$–$C_{12}$alkyl or $C_1$–$C_4$alkoxy, $C_2$–$C_3$alkanoyl or benzoyl, or $R^{20}$ and $R^{21}$ together are $C_2$–$C_8$alkylene, which can be interrupted by —O—, —S— or —$N(R^{17})$—, or can be substituted by hydroxyl, $C_1$–$C_4$alkoxy or —COO($C_1$–$C_4$alkyl) and $R^{22}$ is $C_1$–$C_{18}$alkyl, phenyl which is unsubstituted or substituted by halogen, $C_1$–$C_{12}$alkyl or $C_1$–$C_8$alkoxy or naphthyl, or an acid addition salt of such a compound, in particular compounds of the formula I in which $Ar^1$ is a group of the formula IV, V or VII and $R^1$, $R^2$, $R^3$, $R^4$, $R^5$, $R^6$, $R^7$, $R^8$, $R^9$, $R^{10}$, V, U and W are as defined above.

$C_1$–$C_4$Alkyl $R^{14}$, $R^{15}$ and $R^{16}$ can be, for example, methyl, ethyl, propyl, isopropyl, butyl, isobutyl, sec-butyl or tert-butyl.

$C_1$–$C_8$Alkyl $R^2$, $R^{11}$ and $R^{13}$ can moreover also be, for example, pentyl, hexyl, heptyl, octyl, 2-ethylhexyl or 2,2,4,4-tetramethylbutyl. $C_1$–$C^{12}$Alkyl $R^3$, $R^4$, $R^5$, $R^6$, $R^7$, $R^8$, $R^9$, $R^{10}$, $R^{17}$, $R^{18}$, $R^{19}$, $R^{20}$ and $R^{21}$ can moreover also be, for example, nonyl, decyl, isodecyl, undecyl or dodecyl.

$C_3$–$C_5$Alkenyl $R^3$, $R^4$, $R^1$, $R^{17}$, $R^{20}$ and $R^{21}$ can be, for example, allyl, methallyl, crotyl or dimethylallyl, allyl being preferred. $C_3$–$C_{12}$Alkenyl $R^{18}$ and $R^{19}$ can moreover also be, for example, hexenyl, octenyl or decenyl.

$C_5$–$C_6$Cycloalkyl $R^2$, $R^5$, $R^6$, $R^7$, $R^8$ and $R^9$ are, in particular, cyclohexyl. $C_5$–$C_{12}$Cycloalkyl $R^3$, $R^4$, $R^{20}$ and $R^{21}$ can moreover also be, for example, cyclooctyl or cyclododecyl.

$C_7$–$C_9$Phenylalkyl $R^3$, $R^4$, $R^{17}$, $R^{18}$, $R^{19}$, $R^{20}$ and $R^{21}$ is, in particular, benzyl.

$C_1$–$C_6$Alkylene Y can be, for example, methylene, or di-, tri-, tetra-, penta- or hexamethylene. $C_1$–$C_7$Alkylene W can be, for example, methylene, ethylene, 1,2-propylene or 1,2-hexylene.

$C_2$–$C_6$Alkylidene V and W can be, for example, ethylidene, propylidene, butylidene, isobutylidene or hexylidene.

Examples of $Ar^2$ are the groups phenyl, 1-naphthyl, 2-naphthyl, 2-furyl, 2-thienyl, 3-pyridyl, 4-chlorophenyl, tolyl, 4-isopropylphenyl, 4-octylphenyl, 3-methoxyphenyl, 4-phenoxyphenyl, 4-phenylphenyl, 4-benzoylphenyl, 4-chloro-1-naphthyl and 4-methyl-2-pyridyl.

Examples of substituted alkyl $R^2$ are the groups 2-methoxyethyl, 3-butoxypropyl, 2-isopropoxyethyl, 4-phenoxybutyl, 2-chloroethyl, 3-chloropropyl, 2-phenylethyl or 3-phenylpropyl. Examples of substituted phenyl R² are the groups 4-chlorophenyl, 3-methoxyphenyl, 4-tolyl or 4-butylphenyl.

Substituted alkyl R³ and R⁴ can be, for example, 2-hydroxyethyl, 2-hydroxypropyl, 2-hydroxyisobutyl, 2-ethoxyethyl, 2-methoxypropyl, 2-<-butoxyethyl, 2-cyanoethyl, 2-ethoxycarbonylethyl or 2-methoxycarbonylethyl.

Substituted phenyl R⁴ can be, for example, 3-chlorophenyl, 4-chlorophenyl, 4-tolyl, 4-tert-butylphenyl, 4-dodecylphenyl, 3-methoxyphenyl or 3-methoxycarbonylphenyl.

If R⁴ together with R² is alkylene or phenylalkylene, these preferably give, together with the C atom and the N atom to which they are bonded, a 5- or 6-membered heterocyclic ring.

If R³ and R⁴ together are alkylene or interrupted alkylene, these preferably give, together with the N atom to which they are bonded, a 5-or 6-membered heterocyclic ring, for example a pyrrolidine, piperidine, morpholine, thiomorpholine, piperidone or piperazine ring, which can be substituted by one or more alkyl, hydroxyl, alkoxy or ester groups.

$C_2-C_8$alkanoyl $R^{10}$, $R^{17}$ and $R^{18}$ can be, for example, propionyl, butyryl, isobutyryl, hexanoyl or octanoyl, but in particular acetyl.

$C_1-C_4$Hydroxyalkyl or $C_2-C_4$hydroxyalkyl $R^{11}$, $R^{17}$, $R^{20}$ and $R^{21}$ can be, for example, hydroxymethyl, 2-hydroxyethyl, 2-hydroxypropyl or 4-hydroxybutyl.

Alkylene or interrupted alkylene $R^{12}$ can be, for example, ethylene, tri-, tetra-, penta-, hexa-, octa- or dodecamethylene, 2,2-dimethyltrimethylene, 1,3,3-trimethyltetramethylene, 3-oxa-pentamethylene, 3-oxa-heptamethylene, 4,7-dioxa-decamethylene, 4,9-dioxadodecamethylene, 3,6,9,12-tetraoxa-tetradecamethylene, 4-aza-heptamethylene, 4,7-di(methylaza)-decamethylene or 4-thia-heptamethylene.

If $R^{14}$ and $R^{15}$ together are $C_3-C_7$alkylene, they are, in particular, 1,3- or 1,4-alkylene, for example, 1,3-propylene, 1,3-butylene, 2,4-pentylene, 1,3-hexylene, 1,4-butylene, 1,4-pentylene or 2,4-hexylene.

Substituted phenyl $R^{18}$, $R^{19}$, $R^{20}$ and $R^{21}$ can be, for example, 4-chlorophenyl, 3-chlorophenyl, 4-tolyl, 4-tert-butylphenyl, 4-nonylphenyl, 4-dodecylphenyl, 3-methoxyphenyl or 4-ethoxyphenyl.

An —Si($C_1-C_8$alkyl)$_r$(phenyl)$_{3-r}$ group $R^{18}$ can be, in particular, —Si(CH₃)₃, —Si(phenyl)₂CH₃, —Si(CH₃)₂ phenyl, —Si(CH₃)₂-[C(CH₃)₂CH(CH₃)₂] or —Si(-phenyl)₃.

Substituted $C_1-C_6$alkyl $R^{18}$ can be, for example, 2-hydroxyethyl, 2-methoxyethyl or 2-allyloxyethyl.

Substituted $C_1-C_6$alkyl $R^{19}$ can be, for example, 2-mercaptoethyl, 2-hydroxyethyl, 2-hydroxypropyl, 2-methoxyethyl, -CH₂CH₂OCH₂CH₂CN or —CH₂CH₂OCH₂CH₂COOCH₃.

Alkoxyalkyl $R^{20}$ and $R^{21}$ can be, for example, methoxyethyl, ethoxyethyl, 2-ethoxypropyl, 2-butoxyethyl, 3-methoxypropyl or 2-hexyloxyethyl.

$C_2-C_3$Alkanoyl $R^{20}$ and $R^{21}$ are, in particular, acetyl.

Substituted phenyl or naphthyl $R^{22}$ can be, for example, 4-tolyl, 4-bromophenyl, 3-chlorophenyl, 4-butylphenyl, 4-octylphenyl, 4-decylphenyl, 4-dodecylphenyl, 3-methoxyphenyl, 4-isopropoxyphenyl, 4-butoxyphenyl, 4-octyloxyphenyl, chloronaphthyl, nonylnaphthyl or dodecylnaphthyl.

If $R^{20}$ and $R^{21}$ together are alkylene or interrupted alkylene, this forms, together with the N atom to which it is bonded, a heterocyclic ring, preferably a 5- or 6-membered ring, which can be substituted by alkyl, hydroxyl, alkoxy or ester groups. Examples of such rings are a pyrrolidine, piperidine, 4-hydroxypiperidine, 3-ethoxycarbonylpiperidine, morpholine, 2,6-dimethylmorpholine, piperazine or 4-methylpiperazine ring.

All these compounds have at least one basic amino group and can therefore be converted into the corresponding salts by addition of acids. The acids can be inorganic or organic acids. Examples of such acids are HCl, HBr, H₂SO₄, H₃PO₄, mono- or polycarboxylic acids, for example, acetic acid, oleic acid, succinic acid, sebacic acid, tartaric acid or CF₃COOH, and sulfonic acids, for example, CH₃SO₃H, C₁₂H₂₅SO₃H, p—C₁₂H₂₅—C₆H₄—SO₃H, p—CH₃—C₆H₄—SO₃H or CF₃SO₃H.

Preferred compounds of the formula I are those in which Ar¹ is a group of the formula IV, R⁵ and R⁶ are hydrogen, halogen, $C_1-C_{12}$alkyl or a group —OR¹⁸, —SR¹⁹, —SOR¹⁹, —SO₂—R¹⁹, —N(R²⁰)(R²¹), —NHSO₂R²² or

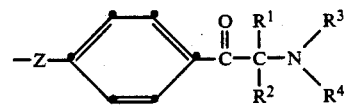

in which Z is —O—, —S—, —N(R¹¹)— or —N(R¹¹)R¹²—N(R¹¹)—, R⁷ and R⁸ are hydrogen or halogen, R⁹ is hydrogen, halogen or $C_1-C_{12}$alkyl and R¹, R², R³, R⁴, R¹¹, R¹², R¹⁸, R¹⁹, R²⁰, R²¹ and R²² are as defined above, and in the case where R¹ is allyl and R² is methyl, R⁵ is not —OCH₃, and in the case where R¹ is benzyl and R² is methyl or benzyl, R⁵ is not —OCH₃, —SCH₃ or —SOCH₃.

Of the compounds of the formula I in which Ar¹ is a group of the formula IV, in which R⁵ is a group —OR¹⁸, —SR¹⁹, —N(R²⁰)(R²¹) or

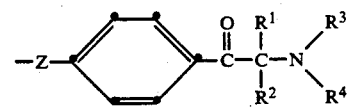

preferred compounds are those in which R⁶ is hydrogen, halogen or $C_1-C_4$-alkyl or has one of the meanings given for R⁵, R⁷ and R⁸ are hydrogen or halogen, R⁹ is hydrogen or $C_1-C_4$alkyl, Z is —O—, —S— or —N(R¹¹)—, R¹ is either (a) a radical of the formula

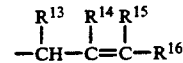

or (b) a radical of the formula —CH(R¹³)—Ar², in which Ar² is a phenyl radical which is unsubstituted or substituted by halogen, $C_1-C_4$alkyl methylthio, methoxy or benzoyl, R² has one of the meanings given for R¹ or is $C_1-C_6$alkyl, R³ and R⁴ independently of one another are $C_1-C_{12}$alkyl, $C_2-C_4$alkyl which is substituted by $C_1-C_4$alkoxy, —CN or —COO($C_1-C_4$alkyl), allyl, cyclohexyl or benzyl, or R³ and R⁴ together are $C_4-C_6$alkylene, which can be interrupted by —O— or —N(R¹⁷)—, R¹¹ is hydrogen, $C_1-C_4$alkyl, allyl, benzyl or $C_2-C_4$alkanoyl, R¹² is $C_2-C_6$alkylene, R¹³, R¹⁴, R¹⁵ and R¹⁶ independently of one another are hydrogen or methyl, R¹⁷ is hydrogen, $C_1-C_4$alkyl, benzyl, 2-hydroxyethyl or acetyl, R¹⁸ is hydrogen, $C_1-C_4$alkyl, 2-hydroxyethyl, 2-methoxyethyl, 2-allyloxyethyl, allyl, cyclohexyl, phenyl, benzyl or —Si(CH$_3$)$_3$, R$^{19}$ is hydrogen, C$_1$–C$_{12}$alkyl, 2-hydroxyethyl, 2-methoxyethyl, phenyl, p-tolyl or benzyl, and R$^{20}$ and R$^{21}$ independently of one another are hydrogen, C$_1$–C$_{12}$alkyl, C$_2$–C$_6$alkoxyalkyl, acetyl, allyl or benzyl, or R$^{20}$ and R$^{21}$ together are C$_4$–C$_6$alkylene, which can be interrupted by —O— or —N(R$^{17}$)—, and, in the case where R$^1$ is allyl, R$^5$ is not —OCH$_3$, and in the case where R$^1$ is benzyl and R$^2$ is methyl or benzyl, R$^5$ is not —OCH$_3$ or —SCH$_3$.

Particularly preferred compounds of the formula I are those in which Ar$^1$ is a group of the formula IV in which R$^5$ is a group —OR$^{18}$, —SR$^{19}$ or —N(R$^{20}$)(R$^{21}$), R$^6$ is hydrogen, chlorine or C$_1$–C$_4$alkyl or has one of the meanings given for R$^5$, R$^7$ and R$^8$ are hydrogen or chlorine, R$^9$ is hydrogen or C$_1$–C$_4$alkyl, R$^1$ is either (a) a radical of the formula —CH$_2$—C(R$^{14}$)=CH(R$^{15}$) or (b) a radical of the formula —CH$_2$-Ar$^2$, in which Ar$^2$ is a phenyl radical which is unsubstituted or substituted by halogen, C$_1$–C$_4$alkyl, CH$_3$S—, CH$_3$O— or benzyl, R$^2$ has one of the meanings given for R$^1$ or is C$_1$–C$_4$alkyl, R$^3$ and R$^4$ independently of one another are C$_1$–C$_6$alkyl, 2-methoxyethyl, allyl or benzyl, or R$^3$ and R$^4$ together are tetramethylene, pentamethylene or 3-oxapentamethylene, R$^{14}$ and R$^{15}$ are hydrogen or methyl, R$^{18}$ is C$_1$–C$_4$alkyl, 2-hydroxyethyl, 2-methoxyethyl or phenyl, R$^{19}$ is C$_1$–C$_{12}$alkyl, 2-hydroxyethyl, 2-methoxyethyl, phenyl or p-tolyl and R$^{20}$ and R$^{21}$ are hydrogen, C$_1$–C$_4$alkyl, 2-methoxyethyl, acetyl or allyl, or R$^{20}$ and R$^{21}$ together are C$_4$–C$_5$-alkylene, alkylene, which can be interrupted by —O— or —N(CH$_3$)—, and in the case where R$^1$ is allyl, R$^5$ is not —OCH$_3$, and in the case where R$^1$ is benzyl and R$^2$ is methyl or benzyl, R$^5$ is not —OCH$_3$ or —SCH$_3$.

Of these compounds, preferred compounds are those in which R$^5$ is a group —SR$^{19}$, R$^1$ is a radical of the formula

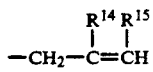

and either R$^7$ and R$^8$ are hydrogen or R$^6$, R$^7$, R$^8$ and R$^9$ are hydrogen, and those in which R$^1$ is allyl.

Of the compounds of the formula I in which Ar$^1$ is a group of the formula IV in which R$^5$ is a group —N(R$^{20}$)(R$^{21}$), compounds which are preferred are those in which R$^7$ and R$^8$ are hydrogen, and those in which R$^6$, R$^7$, R$^8$ and R$^9$ are hydrogen, and those in which R$^1$ is allyl or benzyl.

Preferred compounds of the formula I are moreover those in which Ar$^1$ is a group of the formula IV in which R$^5$ is hydrogen, halogen or C$_1$–C$_{12}$alkyl and R$^6$, R$^7$, R$^8$ and R$^9$ are hydrogen, R$^1$ is allyl or benzyl, R$^2$ is C$_1$–C$_6$alkyl, allyl or benzyl, R$^3$ and R$^4$ independently of one another are C$_1$–C$_{12}$alkyl, C$_2$–C$_4$alkyl which is substituted by C$_1$–C$_4$-alkoxy, —CN or —COO(C$_1$–C$_4$alkyl), allyl, cyclohexyl or benzyl, or R$^3$ and R$^4$ together are C$_4$–C$_6$alkylene, which can be interrupted by —O— or —NR$^{17}$)— and R$^{17}$ is hydrogen, C$_1$–C$_4$alkyl or 2-hydroxyethyl.

Examples of individual compounds of the formula I are:

1. 2-(dimethylamino)-2-ethyl-1-(4-morpholinophenyl)-4-penten-1-one
2. 2-(dimethylamino)-2-methyl-1-(4-morpholinophenyl)-4-penten-1-one
3. 2-benzyl-2-(dimethylamino)-1-(4-morpholinophenyl)-propan-1-one
4. 4-morpholino-4-(4-morpholinobenzyl)-hepta-1,6-diene
5. 2-ethyl-2-morpholino-1-(4-morpholinophenyl)-4-penten-1-one
6. 2-benzyl-2-(dimethylamino)-1-[4-(dimethylamino)-phenyl]-butan-1-one
7. 4-dimethylamino-4-(4-dimethylaminobenzoyl)-hepta-1,6-diene
8. 4-(dimethylamino)-4-(4-morpholinobenzoyl)-hepta-1,6-diene
9. 2-(dimethylamino)-2-(4-dimethylaminophenyl)-2-ethyl-4-penten-1-one
10. 2-benzyl-2-(dimethylamino)-1-(4-morpholinophenyl)-butan 1-one
11. 2-benzyl-2-(dimethylamino)-1-[4-(dimethylamino)-phenyl]-4-penten-1-one
12. 2-benzyl-1-[4-(dimethylamino)-phenyl]-2-(dimethylamino)-3-phenyl-propan-1-one
13. 2-ethyl-1-[4-(methylthio)-phenyl]-2-morpholino-4-penten-1-one
14. 4-[4-(methylthio)-benzoyl]-4-morpholino-hepta-1,6-diene
15. 4-(dimethylamino)-4-(4-methoxybenzoyl)-hepta-1,6-diene
16. 4-(4-methoxybenzoyl)-4-morpholino-hepta-1,6-diene
17. 1-(4-methoxyphenyl)-2-morpholino-2-phenyl-4-penten-1-one
18. 2-ethyl-1-(4-methoxyphenyl)-2-morpholino-4-penten-1-one
19. 2-benzyl-2-(dimethylamino)-1-[4-(methylthio)-phenyl]-butan-1-one
20. 2-(dimethylamino)-2-ethyl-1-[4-(methylthio)-phenyl]-4-penten-1-one
21. 2-benzyl-2-(dimethylamino)-1-[4-(methylthio)-phenyl]-4-penten-1-one
22. 4-(dimethylamino)-4-[4-(methylthio)-benzoyl]-1,6-heptadiene
23. 2-(dimethylamino)-3-(4-fluorophenyl)-2-methyl-1-[4-(methylthio)-phenyl]-propan-1-one
24. 3-(4-chlorophenyl)-2-(dimethylamino)-2-methyl-1-[4-(methylthio)-phenyl]-propan-1-one
25. 3-(2-chlorophenyl)-2-(dimethylamino)-2-methyl-1-[4-(methylthio)-phenyl]-propan-1-one
26. 3-(4-bromophenyl)-2-(dimethylamino)-2-methyl-1-[4-(methylthio)-phenyl]-propan-1-one
27. 2-ethyl-4-methyl-1-[4-(methylthio)-phenyl]-2-morpholino-4-penten 1-one
28. 2-ethyl-1-[4-(methylthio)-phenyl]-2-morpholino-4-hexen-1-one
29. 2-benzyl-1-[4-(methylthio)-phenyl]-2-morpholino-4-penten-1-one
30. 2-allyl-1-[4-(methylthio)-phenyl]-2-morpholino-hexan-1-one
31. 2-(dimethylamino)-1-[4-(methylthio)-phenyl]-2-methyl-3-(4-methyl-phenyl)-propan-1-one
32. 2-(dimethylamino)-1,3-bis-[4-(methylthio)-phenyl]-2-methyl-propan-1-one
33. 2-(dimethylamino)-1-[4-(methylthio)-phenyl]-2-methyl-3-(4-methoxy-phenyl)-propan-1-one
34. 1-[4-(melthio)-phenyl]-2-methyl-2-morpholino-4-penten-1-one
35. 2-(dimethylamino)-1-[4-(methylthio)-phenyl]-2-methyl-4-penten-1-one
36. 1-[4-(methylthio)-phenyl]-2-morpholino-2-phenyl-4-penten-1-one 37. 2-(dimethylamino)-1-[4-(methylthio)-phenyl]-2-phenyl-4-penten-1-one
38. 2-(dimethylamino)-1-[4-(methylthio)-phenyl]-2,3-diphenyl-propan-1-one
39. 2-methyl-2-morpholino-1-(4-morpholinophenyl)-4-penten-1-one
40. 2-benzyl-2-morpholino-1-(4-morpholinophenyl)-4-penten-1-one
41. 2-ethyl-2-morpholino-1-(4-morpholinophenyl)-4-penten-1-one
42. 1-[4-(dimethylamino)-phenyl]-2-methyl-2-morpholino-4-penten-1-one
43. 2-benzyl-2-(dimethylamino)-1-(4-morpholinophenyl)-3-phenyl-propan-1-one
44. 4-[4-(dimethylamino)-benzoyl]-4-morpholino-hepta-1,6-diene
45. 2-(dimethylamino)-1-[4-(dimethylamino)-phenyl]-2-methyl-4-penten-1-one
46. 2-benzyl-2-(dimethylamino)-1-(4-morpholinophenyl)-4-penten-1-one
47. 1-[4-(dimethylamino)-phenyl]-2-ethyl-4-methyl-2-morpholino-4-penten-1-one
48. 1-[4-(dimethylamino)-phenyl]-2-ethyl-2-morpholino-4-hexen-1-one
49. 2-ethyl-2-morpholino-1-(4-morpholinophenyl)-4-hexen-1-one
50. 2-ethyl-4-methyl-2-morpholino-1-(4-morpholinophenyl)-4-penten-1-one
51. 1-[4-(bis-(2-methoxyethyl)amino)-phenyl]-2-methyl-2-morpholino-4-penten-1-one
52. 1-[4-(dibutylamino)phenyl]-2-methyl-2-morpholino-4-penten-1-one
53. 2-methyl-1-[4-(4-methyl-piperazin-1-yl)-phenyl]-2-morpholino-4-penten-1-one
54. 2-benzyl-2-(dimethylamino)-1-(4-methoxyphenyl)-butan-1-one
55. 1-[4-(diethylamino)-phenyl]-2-methyl-2-morpholino-4-penten-1-one
56. 2-methyl-2-morpholino-1-[4-(pyrrolidin-1-yl)-phenyl]-4-penten-1-one
57. 2-benzyl-2-(dimethylamino)-1-(4-piperidinophenyl)-butan-1-one,
58. 2-ethyl-2-(dimethylamino)-1-(4-piperidinophenyl)-4-penten-1-one
59. 2-benzyl-1-[4-(diethylamino)phenyl]-2-ethyl-butan-1-one
60. 1-[4-(diethylamino)phenyl]-2-ethyl-4-penten-1-one
61. 2-benzyl-2-(dimethylamino)-1-[4-(2-hydroxyethylthio)-phenyl]-butan-1-one
62. 2-ethyl-1-[4-(2-hydroxyethylthio)-phenyl]-2-morpholino-4-penten-1-one
63. 1-[4-(diallylamino)-phenyl]-2-methyl-2-morpholino-4-penten-1-one
64. 3-(4-benzoylphenyl)-2-(dimethylamino)-2-methyl-1-[4-(methylthio)-phenyl]-propan-1-one
65. 2-(dimethylamino)-3-(3,4-dimethoxyphenyl)-2-methyl-1-phenyl-propan-1-one
66. 2-(dimethylamino)-3-(3,4-dimethoxyphenyl)-2-methyl-1-[4-(methyl-thio)-phenyl]-propan-1-one
67. 3-(4-benzoylphenyl)-2-(dimethylamino)-2-methyl-1-phenyl-propan-1-one
68. 2-benzyl-2-(dimethylamino)-1-(4-fluorophenyl)-butan-1-one
69. 4-(dimethylamino)-4-(4-fluorobenzoyl)-hepta-1,6-diene
70. 2-ethyl-2-morpholino-1-[4-(4-methylphenylsulfonyl)phenyl]-4-penten-1-one
71. 2-(dimethylamino)-2-ethyl-1-[4-(methylsulfonyl)-phenyl]-4-penten-1-one
72. 2-benzyl-2-(dimethylamino)-1-[4-(methylphenylsulfonyl)phenyl]-butan-1-one
73. 2-benzyl-2-(dimethylamino)-1-[4-methylsulfonyl)-phenyl]-butan-1-one
74. 1-(4-fluorophenyl)-2-methyl-2-morpholino-4-penten-1-one
75. 4-(4-fluorobenzoyl)-4-morpholino-hepta-1,6-diene
76. 2-benzyl-2-(dimethylamino)-1-(4-fluorophenyl)-4-penten-1-one
77. 2-benzyl-2-(dimethylamino)-1-(4-fluorophenyl)-3-phenyl-propan-1-one
78. 2-(dimethylamino)-2-ethyl-1-(4-fluorophenyl)-4-penten-1-one
79. 2-benzyl-1-(4-fluorophenyl)-2-morpholino-4-penten-1-one
80. 2-ethyl-1-(4-fluorophenyl)-2-morpholino-4-penten-1-one
81. 2-benzyl-2-(dimethylamino)-1-(4-fluorophenyl)-propan-1-one
82. 2-(dimethylamino)-1-(4-fluorophenyl)-2-methyl-4-penten-1-one
83. 2-benzyl-2-(dimethylamino)-1-(4-hydroxyphenyl)-butan-1-one
84. 2-benzyl-1-[4-(ethoxycarbonylmethyloxy)phenyl]-2-(dimethylamino)-butan-1-one
85. 2-benzyl-2-(dimethylamino)-1-[4-(2-hydroxyethyloxy)phenyl]-butan-1-one
86. 2-benzyl-1-(4-chlorophenyl)-2-(dimethylamino)-butan-1-one
87. 2-benzyl-1-(4-bromophenyl)-2-(dimethylamino)-butan-1-one
88. 1-(4-bromophenyl)-2-ethyl-2-morpholino-4-penten-1-one
89. 2-ethyl-1-(4-methoxyphenyl)-2-morpholino-3-penten-1-one
90. 2-(dimethylamino)-2-ethyl-1-(4-methoxyphenyl)-4-penten-1-one
91. 2-benzyl-1-[4-(dimethylamino)phenyl]-2-morpholino-4-penten-1-one
92. 2-benzyl-2-(dimethylamino)-1-[4-(dimethylamino)phenyl]-propan-1-one
93. 2-methyl-2-morpholino-1-phenyl-4-penten-1-one
94. 2-benzyl-2-morpholino-1-phenyl-4-penten-1-one
95. 2-(dimethylamino)-2-methyl-1-phenyl-4-penten-1-one
96. 2-benzyl-2-(dimethylamino)-1-phenyl-propan-1-one
97. 4-benzoyl-4-(dimethylamino)-hepta-1,6-diene
98. 2-benzyl-2-(dimethylamino)-1,3-diphenyl-propan-1-one
99. 2-benzyl-2-(dimethylamino)-1-phenyl-4-penten-1-one
100. 2-(dimethylamino)-2-ethyl-1-phenyl-4-penten-1-one
101. 2-benzyl-2-(dimethylamino)-1-phenyl-butan-1-one
102. 1,2-diphenyl-2-morpholino-4-penten-1-one
103. 3-(4-chlorophenyl)-2-(dimethylamino)-2-methyl-1-phenyl-propan-1-one
104. 3-(4-bromophenyl)-2-(dimethylamino)-2-methyl-1-phenyl-propan-1-one
105. 3-(2-chlorophenyl)-2-(dimethylamino)-2-methyl-1-phenyl-propan-1-one
106. 3-(3,4-dimethoxyphenyl)-2-(dimethylamino)-2-methyl-1-phenyl-propan-1-one
107. 2-(dimethylamino)-2-methyl-3-(4-methylphenyl)-1-phenyl-propan-1-one 108. 2-(dimethylamino)-2-methyl-3-[4-(methylthio)-phenyl]-1-phenyl-propan-1-one
109. 2-(dimethylamino)-3-(4-fluorophenyl)-2-methyl-1-phenyl-propan-1-one
110. 2-(dimethylamino)-3-(4methoxy-phenyl)-2-methyl-1-phenyl-propan-1-one
111. 2-ethyl-1-(4-fluorophenyl)-4-methyl-2-morpholino-4-penten-1-one
112. 2-ethyl-1-(4-fluorophenyl)-5-methyl-2-morpholino-4-penten-1-one
113. 2-(benzylmethylamino)-2-ethyl-1-(4-morpholino-phenyl)-4-penten-1-one
114. 2-(allylmethylamino)-2-ethyl-1-(4-morpholino-phenyl)-4-penten-1-one
115. 2-benzyl-2-(benzylmethylamino)-1-(4-morpholino-phenyl)-4-butan-1-one
116. 2-benzyl-2-(butylmethylamino)-1-(4-morpholino-phenyl)-4-butan-1-one
117. 2-(butylmethylamino)-1-(4-morpholinophenyl)-4-penten-1-one
118. 1-(4-acetylaminophenyl)-2-benzyl-2-dimethylamino-butan-1-one
119. 2-benzyl-2-dimethylamino-1-(4-morpholino-phenyl)-pentan-1-one
120. 2-allyl-2-dimethylamino-1-(4-morpholinophenyl)-pentan-1-one
121. 2-morpholino-1-[4-(2-methoxyethyloxy)phenyl]-2-methyl-4-penten-one
122. 4-morpholino-4-[4-(2-hydroxyethylthio)benzoyl]-5-methyl-1-hexene
123. 1-(4-bromophenyl)-2morpholino-2-methyl-4-penten-1-one
124. 4-(4-bromobenzoyl)-4morpholino-5-methyl-1-hexene
125. 1-(4-[2-hydroxyethylthio]phenyl)-2-methyl-2-morpholino-4-penten-1-one
126. 1-(4-[2-(allyloxy)-ethoxy]phenyl)-2-ethyl-2-morpholino-4-penten-1-one
127. 1-(4-[2-(allyloxy)-ethoxy]phenyl)-2-methyl-2morpholino-4-penten-1-one
128. 1-(4-[2-(methoxy)-ethoxy]phenyl)-2-ethyl-2-morpholino-4-penten-1-one
129. 2-benzyl-2-dimethylamino-1-[4-(2-methoxyethylamino)phenyl]-butan-1-one
130. 2-benzyl-2-dimethylamino-1-(4-methylamino-phenyl)-butan-1-one
131. 2-benzyl-2-dimethylamino-1-[4-(N-acetylmethylamino)phenyl]-butan-1-one
132. 2-benzyl-2-diethylamino-1-(4-morpholino-phenyl)-butan-1-one
133. 2-diethylamino-2-ethyl-1-(4-morpholino-phenyl)-4-penten-1-one
140. 2-benzyl-2-(dimethylamino)-1-(3,5-dimethyl-4-methoxy-phenyl)-butan-1-one
141. 2-benzyl-1-(2,4-dichlorophenyl)-2-(dimethylamino)-butan-1-one
142. 2-(dimethylamino)-2-ethyl-1-(3.4-dichlorophenyl)-4-penten-1-one
143. 2-benzyl-1-(3,4-dichlorophenyl)-2-(dimethylamino)-butan-1-one
144. 1-(3-chloro-4-morpholino-phenyl)-2-(dimethylamino)-butan-1-one
145. 2-benzyl-1-(3-chloro-4-morpholino-phenyl)-2-(dimethylamino)-butan-1-one
146. 2-benzyl-2-dimethylamino-1-(4-dimethylamino-3-ethyl-phenyl)-butan-1-one
147. 2-benzyl-2-dimethylamino-1-(4-dimethylamino-2-methyl-phenyl)-butan-1-one
148. 9-butyl-3,6-di(2-benzyl-2-dimethylamino-butyryl)-carbazole
149. 9-butyl-3,6-di(2-methyl-2-morpholino-4-penten-1-on-1-yl)-carbazole
150. 2-benzyl-2-dimethylamino-1-(4-morpholino-phenyl)-butan-1-one-tri-fluoracetate
151. 2-benzyl-2-dimethylamino-1-(4-morpholino-phenyl)-butan-1-one-p-toluenesulfonate
152. 2-benzyl-2-dimethylamino-1-(4-morpholino-phenyl)-butan-1-one-camphorsulfonate
153. 4-(dimethylamino)-4-[4-(phenyloxy)-benzoyl]-hepta-1,6-diene
154. 2-benzyl-2-(dimethylamino)-1-(4-isopropyloxyphenyl)-4-penten-1-one
155. 1-(4-butyloxyphenyl)-2-ethyl-2-morpholino-4-penten-one
156. 1-(4-allyloxyphenyl)-2-benzyl-2-(dimethylamino)-butan-1-one
157. 2-methyl-2-morpholino-1-[4-(trimethylsilyloxy)-phenyl]-4-penten-1-one
158. 2-benzyl-2-(dimethylamino)-1-[4-((1,1,2-trimethylpropyl-dimethyl)-silyloxy)-phenyl]-butan-2-one
159. 2-ethyl-1-[4-(ethylthio)-phenyl]-2-morpholino-4-penten-1-one
160. 2-benzyl-1-[4-(butylthio)-phenyl]-2-(dimethylamino)-3-phenyl-propan-1-one
161. 1-[4-(isopropylthio)-phenyl]-2-methyl-2-morpholino-4-penten-1-one
162. 1-[4-(allylthio)-phenyl]-2-ethyl-2-morpholino-4-penten-1-one
163. 1-[4-(benzylthio)-phenyl]-2-benzyl-2-(dimethylamino)-propan-1-one
164. 2-benzyl-2-(dimethylamino)-1-(4-mercaptophenyl)-butan-1-one
165. 2-benzyl-1-[4-(cyclohexylthio)-phenyl]-2-(dimethylamino)-3-phenyl-propan-1-one
166. 2-ethyl-1-[4-(4-methylphenylthio)-phenyl]-2-morpholino-4-penten-1-one
167. 2-benzyl-2-(dimethylamino)-1-[4-(octylthio)-phenyl]-butan-1-one
168. 2-benzyl-1-[4-(chlorophenylthio)-phenyl]-2-(dimethylamino)-4-penten-1-one
169. 2-methyl-1-[4-(2-methoxycarbonylethylthio)-phenyl]-2-morpholino-4-penten-1-one
170. 1-[4-(butylsulfinyl)-phenyl]-2-(dimethylamino)-2-ethyl-4-penten-1-one
171. 1-[4-(benzenesulfonyl)-phenyl]-2-benzyl-2-(dimethylamino)-butan-1-one
172. 2-benzyl-2-(dimethylamino)-1-[4-(methylsulfinyl)-phenyl]-butan-1-one
173. 2-ethyl-1-[4-(4-methylphenylsulfonyl)-phenyl]-2-morpholino-4-penten-1-one
174. 1-(3,4-dimethoxyphenyl)-2-ethyl-2-morpholino-4-penten-1-one
175. 2-benzyl-1-(3,4-dimethoxyphenyl)-2-(dimethylamino)-butan-1-one
176. 4-(3,4-dimethoxybenzoyl)-4-(dimethylamino)-hepta-1,6-diene
177. 1-(1,3-benzodioxol-5-yl)-2-benzyl-2-(dimethylamino)-butan-1-one
178. 1-(1,3-benzodioxol-5-yl)-2methyl-2-morpholino-4-penten-1-one
179. 2-benzyl-2-(dimethylamino)-1-(3,4,5-trimethoxyphenyl)-butan-1-one
180. 1-(dibenzofuran-3-yl)-2-ethyl-2-morpholino-4-penten-1-one
181. 1-(4-benzoylphenyl)-2-benzyl-2-(dimethylamino)-propan-1-one 182. 2-[2-benzyl-2-(dimethylamino)-butanoyl]-fluorenone
183. 2-(2-methyl-2-morpholino-4-pentenoyl)-xanthone
184. 2-[2-allyl-2-(dimethylamino)-4-pentenoyl]-acridanone
185. 2-[2-benzyl-2-(dimethylamino)-butanoyl]-dibenzosuberone
186. 1-(N-butylcarbazol-3-yl)-2-ethyl-2-morpholino-4-penten-1-one
187. 2-benzyl-1-(N-butylcarbazol-3-yl)-2-(dimethylamino)-butan-1-one
188. 2-allyl-2-(dimethylamino)-1-(N-methylphenothiazin-2-yl)-4-penten-1-one
189. 2-benzyl-1-(N-butyl-phenoxazin-2-yl)-2-morpholino-propan-1-one
190. 2-benzyl-2-(dimethylamino)-1-(xanthen-2-yl)-butan-1-one
191. 1-(chroman-6-yl)-2-ethyl-2-morpholino-4-penten-1-one
192. 2-benzyl-2-(dimethylamino)-1-(N-methylindolin-5-yl)-propan-1-one
193. 1-(N-butylindolin-5-yl)-2-ethyl-2-morpholino-4-penten-1-one
194. 1-(5,10-dibutyl-5,10-dihydrophenazin-6-yl)-2-(dimethylamino)-4-penten-1-one
195. 2-benzyl-1-(1,4-dimethyl-1,2,3,4-tetrahydroquinoxalin-6-yl)-2-(dimethylamino)-butan-1-one
196. 1-(1,4-dibutyl-1,2,3,4-tetrahydroquinoxalin-6-yl)-2-ethyl-2-morpholino-4-penten-1-one
197. 2-benzyl-1-(2,3-dihydro-2,3-dimethyl-benzothiazol-5-yl)-2-(dimethylamino)-butan-1-one
198. 1-(2,3-dihydrobenzofuran-5->1)-2-methyl-2-morpholino-4-penten-1-one
199. 2-benzyl-1-(2,3-dihydrobenzofuran-5-yl)-2-(dimethylamino)-butan-2-one
200. 1-(4-aminophenyl)-2-benzyl-2-(dimethylamino)-butan-2-one
201. 1-[4-(butylamino)phenyl]-2-methyl-2-morpholino-4-penten-1-one
202. 2-benzyl-2-(dimethylamino)-1-[4-(isopropylamino)phenyl]-butan-1-one
203. 2-ethyl-1-(4-methoxyphenyl)-2-piperidino-4-penten-1-one
204. 2-methyl-2-(N-methylpiperazino)-1-[4-(N-methylpiperazino)phenyl]-4-penten-1-one
205. 2-benzyl-2-[di(2-methoxyethyl)-amino]-1-[4-(thiomethyl)phenyl]-butan-1-one
206. 2-(dibutylamino)-1-(4-methoxyphenyl)-2-methyl-4-penten-1-one
207. 1-[4-(dimethylamino)-phenyl]-2-ethyl-2-(methylphenylamino)-4-penten-1-one
208. 2-methyl-1-(methoxyphenyl)-2-oxazolidino-4-penten-1-one
209. 2-ethyl-1-(4-morpholinophenyl)-2-piperidino-4-penten-1-one
200. 2-methyl-2-piperidino-1-(4-piperidinophenyl)-4-penten-1-one
211. 2-ethyl-1-[4-(methylthio)phenyl]-2-piperidino-4-penten-1-one
212. 2-benzyl-2-(dibutylamino)-1-[4-(methylthio)-phenyl]-butan-1-one
213. 2-(dibutylamino)-2-methyl-1-[4-(dimethylamino)-phenyl]-4-penten-1-one
214. 2-benzyl-2-(dibutylamino)-1-(4-morpholinophenyl)-butan-1-one
215. 2-(dimethylamino)-1-[4-(dimethylamino)-phenyl]-2-[(1-cyclo-hexenyl)-methyl]-butan-1-one
216. 2-(dimethylamino)-2-(2-cyclopentenyl)-1-(4-morpholinophenyl)-propan-1-one
217. 2-ethyl-2-(4-morpholinophenyl)—N-methyl-1,2,3,6-tetrahydropyridine
218. 2-(dimethylamino)-1-[4-(dimethylamino)-phenyl]-2,4,5-trimethyl-4-hexen-1-one
219. 2-(dimethylamino)-1-[4-(dimethylamino)-phenyl]-2-(2-pinen-10-yl)-butan-1-one
220. 2-benzyl-2-(dimethylamino)-1-[4-(2,6-dimethylmorpholin-4-yl)-phenyl]-butan-1-one
221. 2-ethyl-2-(2.6-dimethylmorpholin-4-yl)-1-[4-(2,6-dimethylmorpholin-4-yl)phenyl]-4-penten-1-one
222. 1-[4-(dimethylamino)phenyl]-2-ethyl-2-(2,6-dimethylmorpholin-4-yl)-4-penten-1-one
223. 1-[4-(2,6-dimethylmorpholin-4-yl)phenyl]-2-methyl-2-morpholino-4-penten-1-one
224. 2-ethyl-1-[4-(2-hydroxyethoxy)phenyl]-2-morpholino-4-penten-1-one
225. 1-[4-(2-methoxyethyloxy)phenyl]-2-methyl-2-morpholino-4-penten-1-one
226. 1-[4-(2-hydroxyethylthio)phenyl]-2-morpholino-2-propyl-4-penten-1-one
227. 2-benzyl-2-(dimethylamino)-1-[4-(2-methoxyethylthio)phenyl]-butan-1-one
228. 2-(dimethylamino)-2-isopropyl-1-(4-morpholinophenyl)-4-penten-1-one
229. 2-benzyl-1-(3,5-dichlorophenyl)-2-(dimethylamino)-butan-1-one
230. 1-(3,5-dichloro-4-methoxyphenyl)-2-methyl-2-morpholino-4-penten-1-one
231. 2-(diallylamino)-2-ethyl-1-(4-morpholinophenyl)-4-penten-1-one
232. 1-[4-(dimethylamino)phenyl]-2-methyl-2-(pyrrolidin-1-yl)-4-penten-1-one
233. 2-benzyl-2-(dimethylamino)-1-(4-methylphenyl)butan-1-one
234. 1-(4-dodecylphenyl)-2-ethyl-2-morpholino-4-penten-1-one
235. 2-methyl-1-(4-methylphenyl)-2-morpholino-4-penten-1-one
236. Dodecylbenzenesulfonate of 2-ethyl-2-morpholino-1-(4-morpholinophenyl)-4-penten-1-one
237. Dodecylbenzenesulfonate of 2-benzyl-2-(dimethylamino)-1-(4-morpholinophenyl)-butan-1-one.
238. 2-dimethylamino-2-(4-dodecylbenzyl)-1-(4-morpholinophenyl)-butan-1-one
239. 2-(4-ethylbenzyl)-2-dimethylamino-1-(4-morpholinophenyl)-butan-1-one
240. 2-dimethylamino-2-(4-isopropylbenzyl)-1-(4-morpholinophenyl)-butan-1-one
241. 2-dimethylamino-1-(4-dimethylaminophenyl)-1-(4methylbenzyl)-butan-1-one
242. 2-dimethylamino-2-(4-hydroxymethylbenzyl)-1-(4-morpholinophenyl)-butan-1-one
243. 2-(4-[acetoxyethyl]benzyl)-2-dimethylamino-1-(4-morpholino-phenyl)-butan-1-one
244. 2-dimethylamino-2-(4-[2-(2-methoxyethoxy)ethyloxy]benzyl)-1-(4-morpholinophenyl)-butan-1-one
245. 2-dimethylamino-2-(4-[2-(2-[2-methoxyethoxy]ethoxycarbonyl)-ethyl]benzyl)-1-(4-morpholin phenyl)-butan-1-one
246. 2-(4-[2-bromoethyl]benzyl)-2-dimethylamino-1-(4-morpholinophenyl)-butan-1-one
247. 2-(4-[2-diethylaminoethyl]benzyl)-2-dimethylamino-1-(4-morpholinophenyl)-butan-1-one
248. 2-dimethylamino-1-(4-dimethylaminophenyl)-2-(4-dodecylbenzyl)-butan-1-one 249. 2-dimethylamino-1-(4-dimethylaminophenyl)-2-(4-isopropylbenzyl)-butan-1-one
250. 2-dimethylamino-2-(3,4-dimethylbenzyl)-1-(4-morpholinophenyl)-butan-1-one
251. 2-dimethylamino-2-[4-(2-(2-methoxyethoxy)-ethoxycarbonyl)benzyl]-1-(4-morpholinophenyl)-butan-1-one
264. 2-(dimethylamino)-2-(4-methylbenzyl)-1-(4-morpholinophenyl)-butan-1-one
265. 2-(4-butylbenzyl)-2-(dimethylamino)-1-(4-morpholinophenyl)-butan-1-one
266. 2-(dimethylamino)-2-(4-isobutylbenzyl)-1-(4-morpholinophenyl)-butan-1-one
267. 2-benzyl-2-(dimethylamino)-1-(4-[3-methoxypropylamino]phenyl)-butan-1-one
268. 1-(4-[N-acetyl-3-methoxypropylamino]phenyl)-2-benzyl-2-(dimethylamino)-butan-1-one
269. 2-benzyl-2-(di[2-methoxyethyl]amino)-1-(4-morpholinophenyl)-butan-1-one
270. 2-ethyl-2-(di[2-methoxyethyl]amino)-1-(4-morpholinophenyl)-4-penten-1-one
271. 2-benzyl-2-(dimethylamino)-1-(4-morpholinophenyl)-hexan-1-one
272. 2-benzyl-2-(dimethylamino)-1-(4-morpholinophenyl)-heptan-1-one
273. 2-benzyl-2-(dimethylamino)-1-(4-morpholinophenyl)-octan-1-one
274. 2-benzyl-2-(dimethylamino)-4,5,5-trimethyl-1-(4-morpholinophenyl)-hexan-1-one
275. 2-(dimethylamino)-2-(4-methoxybenzyl)-1-(4-morpholinophenyl)-butan-1-one
276. 2-(4-butoxybenzyl)-2-(dimethylamino)-1-(4-morpholinophenyl)-butan-1-one
277. 2-(dimethylamino)-2-(4-[2-hydroxyethoxy]-benzyl)-1-(4-morpholino-phenyl)-butan-1-one
278. 2-(dimethylamino)-2-(4-[2-methoxyethoxy]-benzyl)-1-(4-morpholinophenyl)-butan-1-one
279. 2-(dimethylamino)-2-(4-isopropylbenzyl)-1-(4-morpholinophenyl)-butan-1-one
280. 2-(dimethylamino)-2-(4-dodecylbenzyl)-1-(4-morpholinophenyl)-octan-1-one
281. 2-(dimethylamino)-2-(2-isopropylbenzyl)-1-(4-morpholinophenyl)-pentan-1-one
282. 2-(dimethylamino)-1-(4-(dimethylamino)phenyl-2-(4-[2methoxy]-benzyl)-heptan-1-one
283. 2-(butylmethylamino)-2-(4-isopropylbenzyl)-1-(4-morpholinophenyl)-butan-1-one
284. 2-(4-isobutylbenzyl)-2-(butylmethylamino)-1-(4-morpholinophenyl)-pentan-1-one
285. 2-(4-methylbenzyl)-2-(dioctylamino)-1-(4-morpholinophenyl)-hexan-1-one
286. 2-(4-butoxybenzyl)-2-(butylmethylamino)-1-(4-morpholinophenyl)-pentan-1-one and
287. 2-(4-butylbenzyl)-2-(butylmethylamino)-1-(4-morpholinophenyl)-hexan-1-one.

Examples of individual compounds of the formula II are:
252. N,N'-bis[1-ethyl-1-(4-morpholinobenzoyl)-3-butenyl]-piperazine
253. N,N'-bis[1-allyl-1-(4-(dimethylamino)-benzoyl)-3-butenyl]-piperazine
254. N,N-bis[1-benzyl-1-(4-methoxybenzoyl)-propanyl]-methylamine
255. N,N'-bis[1-ethyl-1-(4-(methylthio)-benzoyl)-butenyl]-hexamethylenediamine.
256. N,N'-bis[1-benzyl-1-(4-morpholinobenzoyl)-propan-1-yl]—N,N'-dimethyl-3,6,9,12-tetraoxa-tetradecamethylenediamine Examples of individual compounds of the formula III are:
257. 1,10-bis[4-dimethylamino)-phenyl]-2,9-diallyl-2,9-dimorpholinodecane-1,10-dione
258. 1,6-bis[4-(methylthio)-phenyl]-2,4-bis(dimethylamino)-2,4-dibenzylhexane-1,6-dione
259. 1,4-bis[2-(dimethylamino)-2-(4-morpholinobenzoyl)-4-pentenyl]-benzene
260. 1,4-bis[2-(dimethylamino)-2-(4-methoxybenzoyl)-3-phenylpropanyl]-benzene.
261. 1,4-bis[2-(dimethylamino)-2-(4-morpholinobenzoyl)-butyl)benzene
262. 3,8-bis(dimethylamino)-3,8-bis(4-morpholinobenzoyl)-dec-5-ene
263. 3,8-bis(dimethylamino)-5,6-dimethylidene-3,8-bis(4-morpholinobenzoyl)-decane In most of these compounds, $R^1$—or $R^1$ and $R^2$—is a substituent of the allyl or benzyl type. The synthesis of such compounds usually includes C-allylation or C-benzylation. The amino group —$NR^3R^4$ is preferably introduced before the allylation/benzylation. The synthesis is then carried out in the following sequence of reaction steps:

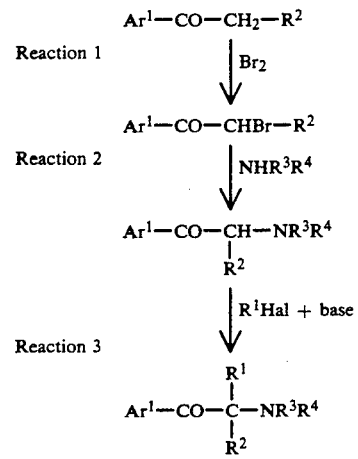

The starting ketones are known compounds which can be prepared, for example, by a Friedel-Crafts reaction. Reaction steps 1 and 2 are known reactions which are described in more detail, for example, in EP-A-3,002. The two reactions can be carried out one after the other without isolating the bromoketone.

Reaction 3 is described in detail below. In the case of C-allylation, it can proceed via the enol allyl ether as an intermediate in the sense of Claisen rearrangement. In the case of C-benzylation or C-allylation, this can proceed via a quaternary benzylammonium salt or allylammonium salt as an intermediate in the sense of a Stevens rearrangement. In both cases, however, the intermediate is not isolated. If both $R^1$ and $R^2$ are allyl or benzyl groups, the above reaction sequence is started with an aryl methyl ketone $Ar^1$—CO—$CH_3$ and reaction 3 is carried out twice, using $R^1$Hal once and $R^2$Hal once.

If the aromatic radical $Ar^1$ carries substituents which are not inert towards reactions 1, 2 or 3, the synthesis is carried out with an auxiliary substituent which is converted into the desired substituent in a subsequent step 4. For example, the syntheses can be carried out with a nitroaryl compound and this can then be reduced to the corresponding amino compound. Alternatively, the synthesis is started with a halogenoaryl compound and the halogen is then replaced by —OR$^{18}$, —SR$^{19}$ or —NR$^{20}$R$^{21}$ in a nucleophilic replacement reaction. A group —SR$^{19}$ can then be oxidized to —SO—R$^{19}$ or —SO$_2$—R$^{19}$.

For synthesis of compounds of the formula II, a primary amine R$^{11}$NH$_2$ or a secondary diamine R$^{11}$—NH—R$^{12}$—NH—R$^{11}$ or piperazine is used in reaction stage 2 and reaction 3) and if appropriate 4) are subsequently carried out.

For synthesis of compounds of the formula III, a bis-aryl ketone of the formula

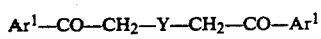

is used as the starting substance and is subjected to reactions 1, 2 and 3.

If R$^1$ is a substituent of the vinyl type, such compounds can be prepared from the corresponding allyl compounds by a catalyzed double bond isomerization. If R$^1$ is a substituent of the formula

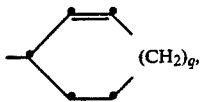

this is introduced in the same way as an allyl radical using a halogen compound of the formula

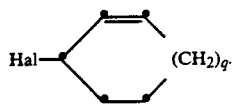

Another possibility for the synthesis of compounds of the formula I is reaction of an α-aminonitrile with an aryl-lithium compound and subsequent hydrolysis:

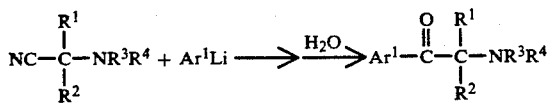

Such reactions have been described, for example, by Cromwell and Hess in J. Am. Chem. Soc. 83, 1237 (1961). The α-aminonitriles are accessible directly by Strecker synthesis from R$^1$—CO—R$^2$, or can be prepared by allylation or benzylation of an α-aminonitrile NC—CHR$^2$—NR$^3$R$^4$. The allylation of α-aminonitriles is described, for example, by T. S. Stevens in J. Chem. Soc. 1930, 2119.

Compounds of the formula I in which R$^1$ and R$^2$ together with the C atom to which they are bonded form a cycloalkene ring can be prepared analogously by reaction of aryl-lithium compounds with the corresponding cyclic nitriles. The cyclic nitriles can be obtained by cycloaddition of α-aminoacrylonitriles onto 1,3-dienes, such as has been described, for example, by Brucher and Stella in Tetrahedron 41, 875 (1985):

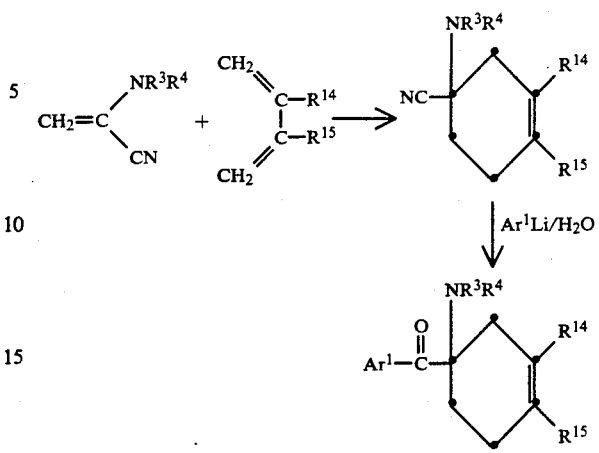

Finally, there is also the possibility of reacting the α-bromoketones with a tertiary allyl- or benzylamine and subjecting the quaternary salt formed to a Stevens rearrangement:

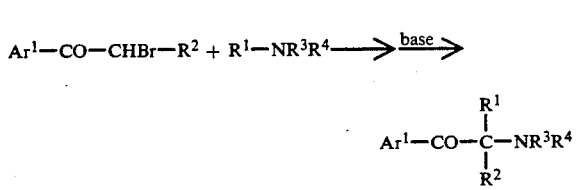

According to the invention, the compounds of the formula I, II and III can be used as photoinitiators for photopolymerization of ethylenically unsaturated compounds or mixtures containing such compounds. The unsaturated compounds can contain one or more olefinic double bonds. They can be of low molecular weight (monomeric) or of higher molecular weight (oligomeric). Examples of monomers with a double bond are alkyl acrylates or methacrylates or hydroxyalkyl acrylates or methacrylates, for example methyl, ethyl, butyl, 2-ethylhexyl or 2-hydroxyethyl acrylate, isobornyl acrylate and methyl or ethyl methacrylate. Further examples of these are acrylonitrile, acrylamide, methacrylamide, N-substituted (meth)acrylamides, vinyl esters, such as vinyl acetate, vinyl ethers, such as isobutyl vinyl ether, styrene, alkyl- and halogenostyrenes, N-vinylpyrrolidone, vinyl chloride or vinylidene chloride.

Examples of monomers with several double bonds are the diacrylates of ethylene glycol, propylene glycol, neopentylglycol, hexamethylene glycol or bisphenol A, 4,4'-bis(2-acryloyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate and tris-(2-acryloyloxyethyl) isocyanurate.

Examples of higher molecular weight (oligomeric) polyunsaturated compounds are acrylated epoxy resins, acrylated polyethers, acrylated polyurethanes and acrylated polyesters. Further examples of unsaturated oligomers are unsaturated polyester resins, which are usually prepared from maleic acid, phthalic acid and one or more diols and have molecular weights of about 500 to 3000. Such unsaturated oligomers can also be called prepolymers.

Two-component mixtures of a prepolymer with a polyunsaturated monomer or three-component mixtures which additionally also contain a monounsaturated monomer are frequently used. The prepolymer here is primarily decisive for the properties of the lacquer film, and by varying it the expert can influence the properties of the cured film. The polyunsaturated monomer functions as crosslinking agents which render the lacquer film insoluble. The monounsaturated monomer functions as reactive diluents, with the aid of which the viscosity is reduced without having to use a solvent.

Such two- and three-component systems based on a prepolymer are used both for printing inks and for lacquers, photoresists or other photocurable compositions. One-component systems based on photocurable prepolymers are frequently also used as binders for printing inks.

Unsaturated polyester resins are usually used in two-component systems together with a monounsaturated monomer, preferably with styrene. Specific one-component systems, for example polymaleimides, polychalcones or polyimides, such as are described in DE-OS 2,308,830, are often used for photoresists.

The unsaturated compounds can also be used as a mixture with non-photo-polymerizable film-forming components. These can be, for example, polymers which dry by physical means and solutions thereof in organic solvents, for example nitrocellulose or cellulose acetobutyrate. They can also be, however, resins which can be cured chemically or thermosetting resins, for example polyisocyanates, polyepoxides or melamine resins. The joint use of thermosetting resins is of importance for use in so-called hybrid systems which are photopolymerized in a first stage and crosslinked by thermal after-treatment in a second stage.

The photopolymerizable mixtures can contain various additives in addition to the photoinitiator. Examples of these are thermal inhibitors for the purpose of preventing premature polymerization, for example hydroquinone or sterically hindered phenols. Copper compounds, phosphorus compounds, quaternary ammonium compounds or hydroxylamine derivatives, for example, can be used to increase the storage stability in the dark. Paraffin or similar waxy substances which migrate to the surface at the start of polymerization can be added for the purpose of excluding atmospheric oxygen during the polymerization. UV absorbers, for example those of the benzotriazole, benzophenone or oxalanilide type, can be added in a small amount as light stabilizers. The addition of light stabilizers which do not absorb UV light, for example sterically hindered amines (HALS), is even better.

In certain cases, it may be advantageous to use mixtures of two or more of the photoinitiators according to the invention. Mixtures with known photoinitiators can, of course, also be used, for example mixtures with benzophenone, acetophenone derivatives, benzoin ethers or benzil ketals.

Amines, for example triethanolamine, N-methyl-diethanolamine, ethyl p-dimethylaminobenzoate or Michler's ketone, can be added to accelerate the photopolymerization. The effect of the amines can be intensified by addition of aromatic ketones of the benzophenone type.

Acceleration of the photopolymerization can furthermore be effected by addition of photosensitizers which shift or extend the spectral sensitivity. These are, in particular, aromatic carbonyl compounds, for example derivatives of benzophenone, thioxanthone, anthraquinone and 3-acylcoumarin, and 3-(aroylmethylene)-thiazolines.

The effectiveness of the photoinitiators according to the invention can be increased by addition of titanocene derivatives with fluoroorganic radicals, such as are described in EP-A-122,223 and 186,626, for example in an amount of 1-20%. Examples of such titanocenes are bis(methylcyclopentadienyl)-bis(2,3,6-trifluorophenyl)-titanium, bis-(cyclopentadienyl)-bis-(4-dibutylamino-2,3,5,6-tetrafluorophenyl)-titanium, bis(methylcyclopentadienyl)-2-(trifluoromethyl)phenyltitanium isocyanate, bis(cyclopentadienyl)-2-(trifluoromethyl)-phenyltitanium trifluoroacetate and bis-(methylcyclopentadienyl)-bis(4-decyloxy-2,3,5,6-tetrafluorophenyl)-titanium. Liquid α-aminoketones are especially suitable for these mixtures.

The photocurable compositions according to the invention can be used for various purposes. Their use in pigmented or coloured systems, for example for printing inks, for photographic reproduction processes, for image recording processes and for producing relief forms, is of particular importance.

Another important field of use are paints, which can be pigmented or non-pigmented. The mixtures are particularly useful in white lacquers, by which is understood paints pigmented with $TiO_2$. Other fields of use are radiation-curing of photoresists, photocrosslinking of silver-free films and production of printing plates. Another use is for external paint films which subsequently harden on their surface in daylight.

The photoinitiators are advantageously used in amounts of 0.1 to 20% by weight, preferably about 0.5 to 5% by weight, based on the photopolymerizable composition, for the fields of use listed.

The polymerization is carried out by the known methods of photopolymerization by irradiation with light rich in short-wavelength radiation. Suitable light sources are, for example, medium-pressure, high-pressure and low-pressure mercury lamps, superactinic tubular lamps and metal halide lamps or lasers with emission maxima in the range between 250 and 450 nm. In the case of combination with photosensitizers or ferrocene derivatives, light of longer wavelengths or laser beams up to 600 nm can also be used.

The preparation and use of the photoinitiators according to the invention are described in more detail in the following examples. In these, parts are parts by weight, percentages are percentages by weight and the temperature is given in degrees Celsius.

EXAMPLE 1

Preparation of an α-benzyl ketone

A) 1-(4-Fluorophenyl)-2-dimethylamino-butan-1-one

240 g (0.98 mol) of 1-(4-fluorophenyl)-2-bromobutan-1-one (prepared by bromination of 4-fluorobutyrophenone by the method described in EP-A-3,002) are dissolved in 250 ml of diethyl ether. This solution is slowly added dropwise to a mixture of 265 g (5.87 mol) of dimethylamine in 1250 ml of diethyl ether at 0°. After the mixture has been stirred at 0° for 12 hours, the excess dimethylamine is removed at room temperature by blowing through $N_2$ and the suspension is poured onto water. The ether phase is washed with water and dried over $MgSO_4$. After filtration and evaporation of the solution, 202.8 g of crude product remain as a colourless oil, which is used without further purification for the subsequent reaction.

The NMR spectrum ($CDCl_3$) of the crude product agrees with the structure given: 7.8–8.23 (m, 2H); 6.8–7.3 (m, 2H); 3.75 (d×d, $^1$H); 2.3 (s, 6H); 1.46–2.3 (m, 2H); 0.83 (t, 3H).

B)
1-(4-Fluorophenyl)-2-dimethylamino-2-benzyl-butan-1-one

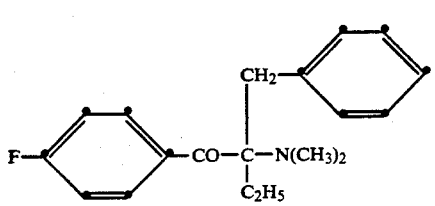

100 g of 1)-2-dimethylamino-butan-1-one (crude product from A) are dissolved in 330 ml of acetonitrile. 98.1 g (0.57 mol) of benzyl bromide are slowly added dropwise, with stirring. After the mixture has been stirred at room temperature for 12 hours, the solvent is distilled off in vacuo. The residue is dissolved in 500 ml of water and the solution is heated to 55°–60°. 113 g of a 34% NaOH solution (0.96 mol) are added dropwise at this temperature and the mixture is subsequently stirred for 30 minutes.

After cooling, the reaction mixture is extracted with diethyl ether and the ether phase is dried over $MgSO_4$ and evaporated. 117.1 g of crude product which is used without further purification for the subsequent reaction remain. The NMR spectrum of the crude product agrees with the structure given.

NMR ($CDCl_3$)— δ(ppm): 8.1–8.53 (m, 2H); 6.76–7.5 (m, 7,H); 3.16 (s, 2H); 2.33 (s, 6H); 1.53–2.2 (m, 2H); 0.65 (t, 3H).

C)
1-(4-Dimethylaminophenyl)-2-dimethylamino-2-benzyl-butan-1-one

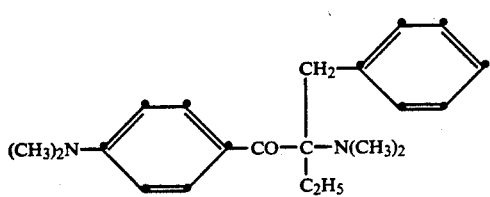

A stirred autoclave is filled with 50 g (0.167 mol) of 1-(4-fluorophenyl)-2-dimethylamino-2-benzylbutan-1-one (crude product from B), 300 ml of dimethylformamide and 23.1 g (0.167 mol) of potassium carbonate. 22.6 g (0.5 mol) of dimethylamine are then added under pressure (3–4 bar). The mixture is heated to 100° and stirred at this temperature for 24 hours.

After cooling, the excess dimethylamine is evaporated off and the reaction mixture is poured onto ice/water and extracted with diethyl ether. The ether phase is washed with water, dried over $MgSO_4$ and evaporated in vacuo. The liquid residue is purified by means of medium-pressure chromatography, ethyl acetate/hexane 15:85 being used as the eluting agent.

44 g of crude product which crystallizes from ethanol are obtained.

Melting point 77°–80°.

| Analysis | Calculated | C 77.74% | H 8.70% | N 8.63% |
|---|---|---|---|---|
| | Found | C 77.59% | H 8.71% | N 8.62% |

Example 2

Preparation of an α-allyl ketone

D)
1-(4-Fluorophenyl)-2-morpholino-2-ethylpent-4-en-1-one

A dispersion of 12.4 g (0.51 mol) of sodium hydride in 50 ml of hexane is diluted with 300 ml of dimethylformamide (DMF). A solution of 117.7 g (0.47 mol) of 1-(4-fluorophenyl)-2-morpholinobutan-1-one in 250 ml of DMF is added dropwise to this suspension in the course of 2 hours, with stirring.

70.8 g (0.58 mol) of allyl bromide are added at room temperature in the course of one hour and the reaction mixture is heated at 110° until no further starting material can be detected in a sample by thin-layer chromatography. After cooling, the reaction mixture is poured onto ice/water and extracted with diethyl ether. The ether phase is dried over $MgSO_4$ and evaporated in vacuo.

127 g of an oily crude product which can be used without further purification for the subsequent reaction are obtained as the residue. The NMR spectrum of the crude product corresponds to the structure given.

NMR ($CDCl_3$), δ(ppm): 8.46 (d×d, 2H); 7 (t, 2H); 4.8–6.5 (m, 3H); 3.5–3.9 (m, 4H); 2.4–3.2 (m, 6H); 1.7–2.3 (m, 2H); 0.75 (t, 3H).

Example 3

Amination of the nucleus under normal pressure

E)
2-Benzyl-2-dimethylamino-1-(4-morpholinophenyl)-butan-1-one 608.7 g (2.03 mol) of 1-(4-fluorophenyl)-2-dimethylamino-2-benzyl-butan-1-one (Example 1, B), 354.2 g (4.06 mol) of morpholine, 562 g (4.06 mol) of $K_2CO_3$ and 2000 ml of dimethylsulfoxide are heated at 160° for 12 hours, with stirring. After this time, a sample no longer shows any starting ketone in a thin-layer chromatogram. The reaction solution is cooled to room temperature, poured onto ice and extracted with methylene chloride. The organic phase is dried over $MgSO_4$, filtered and evaporated. The oily residue crystallizes from ethanol. The product melts at 111°–119°.

| Analysis | Calculated | C 75.37% | H 8.25% | N 7.64% |
|---|---|---|---|---|
| | Found | C 75.40% | H 8.27% | N 7.63% |

EXAMPLE 4

Preparation of a diallyl ketone

F)
2-Dimethylamino-1-(4-(fluorophenyl)-4-penten-1-one

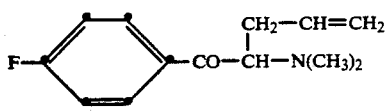

118 g (0.65 mol) of α-dimethylamino-4-fluoroacetophenone are dissolved in 350 ml of acetonitrile. 94.5 g (0.78 mol) of allyl bromide are slowly added dropwise to this solution at about 25° and the reaction mixture is stirred at room temperature for 12 hours. The solvent is evaporated off in vacuo and the solid residue is dissolved in warm water (about 60°). After slow addition of 169 ml of 30% aqueous NaOH (1.27 mol) and cooling to room temperature, the mixture is extracted with diethyl ether. The ether phase is dried and evaporated. The residue obtained is crude 2-dimethylamino-1-(4-fluorophenyl)-4-penten-1-one in the form of an oil, which is used without further purification for the subsequent reaction. The NMR spectrum of the product is in good agreement with the structure given: 7.83–8.23 m (2H, $H_B$), 6.9–7.26 m (2H, $H_A$), 4.76–6.0 m (3H, $H_{olefin}$), 3.96 d×d (1H, J=6 Hz, J=8.5 Hz, Hc), 2.2–2.7 m (2H, $H_D$), 2.3s (6H, $H_E$).

G)
4-Dimethylamino-4-(4-fluorobenzoyl)-hepta-1,6-diene

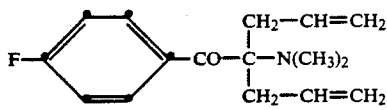

131 g (0.59 mol) of the crude product from F) in 350 ml of acetonitrile and 85.9 g (0.71 mol) of allyl bromide are reacted as in F). Neutralization of the reaction mixture is carried out with 160 ml of 30% NaOH (1.2 mol). The crude product is likewise isolated as in F). The reaction product is a yellowish oil which can be used without further purification for the next stage (amination of the nucleus).

NMR (CDCl$_3$): 8.53–8.1 m (2H, $H_B$), 7.2–6.7 m (2H, $H_A$), 6.1–4.7 m (6H, $H_{olefin}$), 2.8–2.5 m (4H, $H_{allyl}$), 2.4s (6H, N—CH$_3$)

Example 5

Synthesis of 3,6-dibutyryl-9-butyl-9H-carbazole

H) Synthesis of N-butylcarbazole

A suspension of 100 g (0.6 mol) of carbazole in 200 ml of toluene is heated under reflux, with stirring. After cooling to 95°, first 26.8 g (0.12 mol) of triethylbenzylammonium chloride and then a solution of 169.8 g of KOH in 180 ml of water are added. The temperature thereby drops to 65°. 205.6 g (1.5 mol) of butyl bromide are now added in the course of 5 minutes, with vigorous stirring, whereupon the temperature rises to 92°. The mixture is kept under reflux for a further 10 minutes, all the carbazole dissolving. The aqueous phase is then removed. .The toluene phase is washed with a little water, dried over Na$_2$CO$_3$ and evaporated in vacuo. The oily residue is dissolved in 300 ml of warm hexane and the solution is clarified. On cooling, the product crystallizes in beige-coloured crystals of melting point 50°–52°.

I) Friedel-Crafts reaction 46.9 g (0.44 mol) of butyryl chloride are added dropwise to a suspension of 93.3 g (0.7 mol) of AlCl$_3$ in 100 ml of methylene chloride in the course of 30 minutes, while stirring and cooling to −10° to −5°. A solution of 22.3 g (0.1 mol) of N-butylcarbazole in 50 ml of CH$_2$Cl$_2$ is then added dropwise at −10° to −5° in the course of 2 hours. The suspension is stirred at 0° to 20° for 16 hours and then poured onto ice. The emulsion formed is extracted twice with CHCl$_3$ and the extract is washed with water, dried over MgSO$_4$ and evaporated. The crude 3,6-dibutyryl-9-butyl-9H-carbazole is re-crystalized from 80 ml of ethanol. The resulting crystals have a melting point of 107°–109°.

3,6-Dipropionyl-9-butyl-9H-carbazole, which has a melting point of 142°–144°, is obtained in an analogous manner from 81.4 g of propionyl chloride and 44.7 g of N-butylcarbazole.

The products listed in the following tables are prepared analogously to the general Preparation Examples A–I.

TABLE 1

R⁵—[phenyl]—CO—C(R¹)(R²)—NR³R⁴

| Compound No. | R⁵ | R¹ | R² | —NR³R⁴ | Physical properties | | Analysis C | H | N | S |
|---|---|---|---|---|---|---|---|---|---|---|
| 1 | morpholino | Allyl | Ethyl | —N(CH₃)₂ | m.p. 58–61° | calc.<br>found | 72.11<br>72.08 | 8.85%<br>8.73% | | |
| 2 | morpholino | Allyl | Methyl | —N(CH₃)₂ | oil | calc.<br>found | 71.49<br>71.56 | 8.67<br>8.64 | 9.25%<br>9.04% | |
| 3 | morpholino | Benzyl | Methyl | —N(CH₃)₂ | m.p. 90–92° | calc.<br>found | 74.97<br>75.09 | 8.01<br>8.09 | 7.95%<br>7.71% | |
| 4 | morpholino | Allyl | Allyl | morpholino | oil | calc.<br>found | 71.32<br>71.24 | 8.16<br>8.12 | 7.56%<br>7.57% | |
| 5 | morpholino | Allyl | Ethyl | morpholino | oil | calc.<br>found | 70.36<br>69.87 | 8.43<br>8.41 | 7.81%<br>7.64% | |
| 6 | (CH₃)₂N— | Benzyl | Ethyl | —N(CH₃)₂ | m.p. 77–80° | calc.<br>found | 77.74<br>77.59 | 8.70<br>8.71 | 8.63%<br>8.62% | |
| 7 | (CH₃)₂N— | Allyl | Allyl | —N(CH₃)₂ | oil | calc.<br>found | 75.48<br>75.48 | 9.15<br>9.25 | 9.78%<br>9.48% | |
| 8 | morpholino | Allyl | Allyl | —N(CH₃)₂ | m.p. 65–67° | calc.<br>found | 73.14<br>73.05 | 8.59<br>8.51 | 8.59%<br>8.51% | |
| 9 | (CH₃)₂N— | Allyl | Ethyl | —N(CH₃)₂ | m.p. 34–37° | calc.<br>found | 74.41<br>74.29 | 9.55<br>9.55 | 10.21%<br>10.23% | |
| 10 | morpholino | Benzyl | Ethyl | —N(CH₃)₂ | m.p. 110–119° | calc.<br>found | 75.37<br>75.38 | 8.25<br>8.32 | 7.64%<br>7.62% | |
| 11 | (CH₃)₂N— | Benzyl | Allyl | —N(CH₃)₂ | m.p. 68–70° | calc.<br>found | 78.53<br>78.54 | 8.39<br>8.38 | 8.33%<br>8.10% | |

TABLE 1-continued

Structure: R⁵—[phenyl ring]—CO—C(R¹)(R²)—NR³R⁴

| Compound No. | R⁵ | R¹ | R² | —NR³R⁴ | Physical properties | | C | H | N | S |
|---|---|---|---|---|---|---|---|---|---|---|
| 12 | (CH₃)₂N— | Benzyl | Benzyl | —N(CH₃)₂ | m.p. 132–133° | calc. | 80.79 | 7.82 | 7.25% | |
| | | | | | | found | 80.71 | 7.91 | 7.21% | |
| 13 | CH₃S— | Allyl | Ethyl | —N(CH₃)₂ | oil | calc. | 67.68 | 7.89 | 4.38% | |
| | | | | | | found | 67.43 | 7.81 | 4.22% | |
| 14 | CH₃S— | Allyl | Allyl | morpholino | oil | calc. | 68.85 | 7.61 | 4.23% | |
| | | | | | | found | 68.83 | 7.56 | 4.17% | |
| 15 | CH₃O— | Allyl | Allyl | morpholino | oil | calc. | 74.69 | 8.48 | 5.12% | |
| | | | | | | found | 74.54 | 8.48 | 5.04% | |
| 16 | CH₃O— | Allyl | Allyl | —N(CH₃)₂ | oil | calc. | 72.35 | 7.99 | 4.44% | |
| | | | | | | found | 72.51 | 8.09 | 4.14% | |
| 17 | CH₃O— | Allyl | Phenyl | morpholino | m.p. 84–86° | calc. | 75.19 | 7.17 | 3.99% | |
| | | | | | | found | 74.97 | 7.14 | 3.91% | |
| 18 | CH₃O— | Allyl | Ethyl | morpholino | oil | calc. | 71.26 | 8.30 | 4.62% | |
| | | | | | | found | 71.19 | 8.44 | 4.57% | |
| 19 | CH₃S— | Benzyl | Ethyl | —N(CH₃)₂ | oil | calc. | 73.35 | 7.69 | 4.28 | 9.79% |
| | | | | | | found | 73.47 | 7.69 | 4.12 | 9.61% |
| 20 | CH₃S— | Allyl | Ethyl | —N(CH₃)₂ | oil | calc. | 69.27 | 8.35 | 5.05 | 11.55% |
| | | | | | | found | 69.24 | 8.41 | 5.00 | 11.41% |
| 21 | CH₃S— | Allyl | Benzyl | —N(CH₃)₂ | oil | calc. | 74.29 | 7.42 | 4.12 | 9.44% |
| | | | | | | found | 74.22 | 7.44 | 3.92 | 9.26% |
| 22 | CH₃S— | Allyl | Allyl | —N(CH₃)₂ | oil | calc. | 70.55 | 8.01 | 4.82 | 11.08% |
| | | | | | | found | 70.58 | 8.00 | 4.70 | 10.93% |
| 23 | CH₃S— | 4-Fluorobenzyl | Methyl | —N(CH₃)₂ | oil | calc. | 68.89 | 6.69 | 4.22 | 9.67% |
| | | | | | | found | 68.85 | 6.84 | 4.06 | 9.57% |
| 24 | CH₃S— | Methyl | —N(CH₃)₂ | 4-Chlorobenzyl | m.p. 69–70° | calc. | 65.60 | 6.37 | 9.22% | |
| | | | | | | found | | 4.03 | | |
| 25 | CH₃S— | 2-Chlorobenzyl | Methyl | —N(CH₃)₂ | oil | calc. | 65.30 | 6.34 | 3.92 | 9.25% |
| | | | | | | found | 65.59 | 6.37 | 4.03 | 9.22% |
| 26 | CH₃S— | 4-Bromobenzyl | Methyl | —N(CH₃)₂ | oil | calc. | 65.98 | 6.51 | 3.97 | 9.09% |
| | | | | | | | 58.16 | 5.65 | 3.57 | 8.17% |

TABLE 1-continued $$R^5-\phenyl-CO-C(R^1)(R^2)-CO-NR^3R^4$$

| Compound No. | R⁵ | R¹ | R² | —NR³R⁴ | Physical properties | | C | H | N | S |
|---|---|---|---|---|---|---|---|---|---|---|
| 27 | CH₃S— | Methallyl | Ethyl | morpholino | oil | found<br>calc.<br>found | 58.35<br>68.43<br>68.41 | 5.71<br>8.16<br>8.28 | 3.44<br>4.20<br>3.93 | 7.99%<br>9.61%<br>9.53% |
| 28 | CH₃S— | 2-Butenyl | Ethyl | morpholino | oil | calc.<br>found | 68.43<br>68.46 | 8.16<br>8.20 | 4.20<br>4.08 | 9.61%<br>9.53% |
| 29 | CH₃S— | Allyl | Benzyl | morpholino | oil | calc.<br>found | 72.40<br>72.51 | 7.13<br>7.31 | 3.67<br>3.52 | 8.40%<br>8.25% |
| 30 | CH₃S— | Allyl | Butyl | morpholino | oil | calc.<br>found | 69.12<br>68.98 | 8.41<br>8.29 | 4.03<br>3.80 | 9.23%<br>9.26% |
| 31 | CH₃S— | 4-Methylbenzyl | Methyl | —N(CH₃)₂ | m.p. 74–75° | calc.<br>found | 73.35<br>72.84 | 7.69<br>7.72 | 4.28<br>4.29 | 9.79%<br>9.66% |
| 32 | CH₃S— | 4-Methylthiobenzyl | Methyl | —N(CH₃)₂ | oil | calc.<br>found | 66.81<br>66.70 | 7.01<br>7.17 | 3.89<br>3.69 | 17.83%<br>17.41% |
| 33 | CH₃S— | 4-Methoxybenzyl | Methyl | —N(CH₃)₂ | oil | calc.<br>found | 69.93<br>69.50 | 7.34<br>7.38 | 4.08<br>3.84 | 9.33%<br>9.49% |
| 34 | CH₃S— | Allyl | Methyl | pyrrolidino | oil | calc.<br>found | 66.85<br>66.92 | 7.59<br>7.60 | 4.59<br>4.53 | 10.50%<br>10.50% |
| 35 | CH₃S— | Allyl | Methyl | pyrrolidino | oil | calc.<br>found | 68.40<br>68.09 | 8.04<br>8.07 | 5.32<br>5.32 | 12.17%<br>12.16% |
| 36 | CH₃S— | Allyl | Phenyl | morpholino | m.p. 97–99° | calc.<br>found | 71.90<br>71.76 | 6.86<br>7.00 | 3.81<br>3.70 | 8.72%<br>8.74% |
| 37 | CH₃S— | Allyl | Phenyl | —N(CH₃)₂ | oil | calc.<br>found | 73.81<br>73.36 | 7.12<br>7.10 | 4.30<br>4.05 | 9.85%<br>9.78% |
| 38 | CH₃S— | Benzyl | Phenyl | —N(CH₃)₂ | m.p. 142–143° | calc.<br>found | 76.76<br>76.95 | 6.71<br>6.75 | 3.73<br>3.77 | 8.54%<br>8.50% |

TABLE 1-continued

![Structure: R5-C6H4-CO-C(R1)(R2)-NR3R4]

| Compound No. | R5 | R1 | R2 | —NR3R4 | Physical properties | | Analysis C | H | N | S |
|---|---|---|---|---|---|---|---|---|---|---|
| 39 | morpholino | Allyl | Methyl | morpholino | oil | calc.<br>found | 69.74<br>69.43 | 8.19<br>8.33 | 8.13%<br>7.87% | |
| 40 | morpholino | Allyl | Benzyl | morpholino | m.p. 150° | calc.<br>found | 74.26<br>74.22 | 7.67<br>7.66 | 6.66%<br>6.68% | |
| 41 | (CH3)2N— | Allyl | Ethyl | morpholino | oil | calc.<br>found | 72.12<br>72.14 | 8.92<br>8.95 | 8.85%<br>8.62% | |
| 42 | (CH3)2N— | Allyl | Methyl | morpholino | waxy | calc.<br>found | 71.49<br>71.51 | 8.67<br>8.72 | 9.26%<br>9.12% | |
| 43 | morpholino | Benzyl | Benzyl | —N(CH3)2 | m.p. 177–178° | calc.<br>found | 78.47<br>78.57 | 7.53<br>7.59 | 6.54%<br>6.47% | |
| 44 | (CH3)2N— | Allyl | Allyl | morpholino | oil | calc.<br>found | 73.14<br>73.42 | 8.59<br>8.84 | 8.53%<br>7.83% | |
| 45 | (CH3)2N— | Allyl | Methyl | —N(CH3)2 | oil | calc.<br>found | 73.81<br>73.41 | 9.29<br>9.06 | 10.76%<br>9.65% | |
| 46 | (CH3)2N— | Allyl | Benzyl | —N(CH3)2 | m.p. 91–93° | calc.<br>found | 76.16<br>76.27 | 7.99<br>8.04 | 7.40%<br>7.12% | |
| 47 | (CH3)2N— | Methallyl | Ethyl | morpholino | m.p. 79–84° | calc.<br>found | 72.69<br>72.57 | 9.15<br>9.24 | 8.48%<br>8.49% | |

TABLE 1-continued $$R^5\text{-}C_6H_4\text{-}CO\text{-}C(R^1)(R^2)\text{-}NR^3R^4$$

| Compound No. | R¹ | R² | —NR³R⁴ | R⁵ | Physical properties | | Analysis C | H | N | S |
|---|---|---|---|---|---|---|---|---|---|---|
| 48 | 2-Butenyl | Ethyl | morpholino | (CH₃)₂N— | oil | calc.<br>found | 72.69<br>72.12 | 9.15<br>9.17 | 8.48%<br>7.99% | |
| 49 | 2-Butenyl | Ethyl | morpholino | morpholino | oil | calc.<br>found | 70.93<br>70.61 | 8.66<br>8.75 | 7.52%<br>6.93% | |
| 50 | Methallyl | Ethyl | morpholino | (CH₃OCH₂CH₂)₂N— | oil | calc.<br>found | 70.93<br>70.42 | 8.66<br>8.71 | 7.52%<br>7.11% | |
| 51 | Allyl | Methyl | morpholino | (C₄H₉)₂N— | oil | calc.<br>found | 67.66<br>67.81 | 8.78<br>8.76 | 7.17%<br>7.25% | |
| 52 | Allyl | Methyl | morpholino | 4-methylpiperazino | oil | calc.<br>found | 74.57<br>74.62 | 9.91<br>9.87 | 7.25%<br>7.30% | |
| 53 | Allyl | Methyl | morpholino | CH₃O— | oil | calc.<br>found | 70.55<br>70.27 | 8.74<br>8.81 | 11.75%<br>11.64% | |
| 54 | Benzyl | Ethyl | —N(CH₃)₂ | (C₂H₅)₂N— | oil | calc.<br>found | 77.13<br>77.09 | 8.09<br>8.15 | 4.50%<br>4.47% | |
| 55 | Allyl | Methyl | morpholino | (C₂H₅)₂N— | oil | calc.<br>found | 72.69<br>72.66 | 9.15<br>9.15 | 8.48%<br>8.24% | |
| 56 | Allyl | Methyl | morpholino | pyrrolidino | m.p. 98–99° | calc.<br>found | 73.14<br>73.10 | 8.59<br>8.59 | 8.53%<br>8.48% | |

TABLE 1-continued

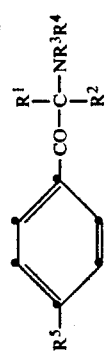

| Compound No. | R⁵ | R¹ | R² | —NR³R⁴ | Physical properties | | Analysis C | H | N | S |
|---|---|---|---|---|---|---|---|---|---|---|
| 57 | (morpholino) | Benzyl | Ethyl | —N(CH₃)₂ | m.p. 76–81° | calc. found | 79.08 78.96 | 8.85 8.79 | 7.68% 7.60% | |
| 58 | (morpholino) | Allyl | Ethyl | —N(CH₃)₂ | oil | calc. found | 76.39 76.40 | 9.62 9.50 | 8.90% 8.74% | |
| 59 | (C₂H₅)₂N— | Benzyl | Ethyl | —N(CH₃)₂ | oil | calc. found | 78.36 77.79 | 9.15 9.08 | 7.95% 7.14% | |
| 60 | (C₂H₅)₂N— | Allyl | Ethyl | —N(CH₃)₂ | oil | calc. found | 75.45 75.35 | 9.99 9.80 | 9.26% 8.70% | |
| 61 | HOCH₂CH₂S— | Benzyl | Ethyl | —N(CH₃)₂ | oil | calc. found | 70.55 70.18 | 7.61 7.51 | 3.92 3.71 | 8.97% 8.95% |
| 62 | HOCH₂CH₂S— | Allyl | Ethyl | —N(CH₃)₂ | oil | calc. found | 65.30 64.54 | 7.79 7.76 | 4.01 3.79 | 9.17% 9.35% |
| 63 | (CH₂=CH—CH₂)₂N— | Allyl | Methyl | (morpholino carbonyl) | oil | | | | | |
| 64 | CH₃S— | 4-Benzoylbenzyl | Methyl | —N(CH₃)₂ | m.p. 135–136° | calc. found | 74.79 74.53 | 6.52 6.56 | 3.35 3.24 | 7.68% 7.55% |
| 65 | H | 3,4-Dimethoxybenzyl | Methyl | —N(CH₃)₂ | m.p. 116–117° | calc. found | 73.36 73.03 | 7.69 7.73 | 4.27% 4.11% | |
| 66 | CH₃S— | 3,4-Dimethoxybenzyl | Methyl | —N(CH₃)₂ | oil | calc. found | 67.53 67.41 | 7.29 7.32 | 3.75 4.03 | 8.58% 8.99% |
| 67 | H | 4-Benzoylbenzyl | Methyl | —N(CH₃)₂ | m.p. 106–108° | calc. found | 80.83 80.22 | 6.78 6.75 | 3.77% 3.79% | |
| 68 | F | Benzyl | Ethyl | —N(CH₃)₂ | m.p. 62–65° | calc. found | 76.22 76.07 | 7.41 7.40 | 4.68% 4.60% | |
| 69 | F | Allyl | Allyl | (morpholino carbonyl) | oil | calc. found | 67.42 66.98 | 6.48 7.10 | 3.28 3.12 | 7.50% 7.51% |
| 70 | F | Allyl | Ethyl | | vitreous | | | | | |
| 71 | CH₃SO₂— (4-CH₃ phenyl) CH₃SO₂— | Allyl | Ethyl | —N(CH₃)₂ | m.p. 74–75° | calc. found | 62.11 62.03 | 7.49 7.48 | 4.53 4.50 | 10.36% 10.27% |

TABLE 1-continued

R⁵—[benzene ring]—CO—C(R¹)(R²)—NR³R⁴

| Compound No. | R⁵ | R¹ | R² | —NR³R⁴ | Physical properties | | Analysis C | H | N | S |
|---|---|---|---|---|---|---|---|---|---|---|
| 72 | 4-CH₃-C₆H₄-SO₂— | Benzyl | Ethyl | —N(CH₃)₂ | m.p. 107–108° | calc. found | 71.69 71.46 | 6.71 6.68 | 3.22 3.16 | 7.36% 7.39% |
| 73 | CH₃SO₂— | Benzyl | Ethyl | —N(CH₃)₂ | vitreous | calc. found | 66.82 66.74 | 7.01 7.01 | 3.90 3.81 | 8.92% 8.94% |
| 74 | F | Allyl | Methyl | morpholino | oil | calc. found | 69.29 69.02 | 7.27 7.47 | 5.05% 4.86% | |
| 75 | F | Allyl | Allyl | morpholino | oil | calc. found | 71.26 71.19 | 7.31 7.25 | 4.62% 4.50% | |
| 76 | F | Allyl | Benzyl | —N(CH₃)₂ | oil | | | | | |
| 77 | F | Benzyl | Benzyl | —N(CH₃)₂ | oil | | | | | |
| 78 | F | Allyl | Ethyl | —N(CH₃)₂ | oil | | | | | |
| 79 | F | Allyl | Benzyl | —N(CH₃)₂ | oil | | | | | |
| 80 | F | Allyl | Ethyl | morpholino | oil | | | | | |
| 81 | F | Benzyl | Methyl | —N(CH₃)₂ | oil | | | | | |
| 82 | F | Allyl | Methyl | —N(CH₃)₂ | oil | | | | | |
| 83 | HO— | Benzyl | Ethyl | —N(CH₃)₂ | m.p. 110–119° | calc. found | 72.04 72.00 | 7.62 7.62 | 3.65% 3.57% | |
| 84 | C₂H₅OOCCH₂O— | Benzyl | Ethyl | —N(CH₃)₂ | oil | calc. found | 73.87 73.83 | 7.97 8.09 | 4.10% 3.82% | |
| 85 | HOCH₂CH₂O— | Benzyl | Ethyl | —N(CH₃)₂ | oil | calc. found | 72.25 72.32 | 7.02 7.03 | 4.43% 4.34% | |
| 86 | Cl | Benzyl | Ethyl | —N(CH₃)₂ | m.p. 67–69° | | | | | |
| 87 | Br | Benzyl | Ethyl | —N(CH₃)₂ | m.p. 53–55° | calc. found | 63.34 63.22 | 6.15 6.19 | 3.89% 3.87% | |

TABLE 1-continued

![structure: benzene ring with R5 substituent and CO-C(R1)(R2)-NR3R4 group]

| Compound No. | R⁵ | R¹ | R² | —NR³R⁴ | Physical properties | | Analysis C | H | N | S |
|---|---|---|---|---|---|---|---|---|---|---|
| 88 | Br | Allyl | Ethyl | morpholino | oil | calc.<br>found | 57.96<br>58.42 | 6.30<br>6.42 | 3.98%<br>3.94% | |
| 89 | CH₃O— | 1-Propenyl | Ethyl | morpholino | oil | calc.<br>found | 71.26<br>71.31 | 8.31<br>8.31 | 4.62%<br>4.42% | |
| 90 | CH₃O— | Allyl | Ethyl | morpholino | oil | calc.<br>found | 76.16<br>76.17 | 7.99<br>7.98 | 7.40%<br>7.13% | |
| 91 | (CH₃)₂N— | Allyl | Benzyl | —N(CH₃)₂ | oil | | | | | |
| 92 | (CH₃)₂N— | Benzyl | Methyl | morpholino | m.p. 107–108° | calc.<br>found | 74.10<br>74.28 | 8.16<br>8.37 | 5.40%<br>5.31% | |
| 93 | H | Allyl | Methyl | —N(CH₃)₂ | liquid | | | | | |
| 94 | H | Allyl | Benzyl | morpholino | oil | calc.<br>found | 78.77<br>78.82 | 7.51<br>7.76 | 4.11%<br>3.73% | |
| 95 | H | Allyl | Methyl | —N(CH₃)₂ | liquid | calc.<br>found | 77.40<br>77.34 | 8.80<br>8.79 | 6.45%<br>6.41% | |
| 96 | H | Benzyl | Methyl | —N(CH₃)₂ | liquid | calc.<br>found | 80.86<br>80.80 | 7.92<br>8.06 | 5.24%<br>5.17% | |
| 97 | H | Allyl | Allyl | —N(CH₃)₂ | oil | calc.<br>found | 79.97<br>78.77 | 8.70<br>8.75 | 5.76%<br>5.64% | |
| 98 | H | Benzyl | Benzyl | —N(CH₃)₂ | oil | calc.<br>found | 81.87<br>81.70 | 7.90<br>7.84 | 4.77%<br>4.65% | |
| 99 | H | Allyl | Benzyl | —N(CH₃)₂ | oil | | | | | |
| 100 | H | Allyl | Ethyl | —N(CH₃)₂ | liquid | calc.<br>found | 77.88<br>77.85 | 9.15<br>9.17 | 6.05%<br>6.01% | |
| 101 | H | Benzyl | Ethyl | —N(CH₃)₂ | oil | calc.<br>found | 81.10<br>81.14 | 8.24<br>8.45 | 4.98%<br>4.93% | |

TABLE 1-continued

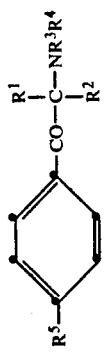

| Compound No. | R⁵ | R¹ | R² | —NR³R⁴ | Physical properties | | Analysis C | H | N | S |
|---|---|---|---|---|---|---|---|---|---|---|
| 102 | H | Allyl | Phenyl | —N(morpholino) | m.p. 87–88° | calc. found | 78.47 78.17 | 7.21 7.10 | 4.36% 4.32% | |
| 103 | H | 4-Chlorobenzyl | Methyl | —N(CH₃)₂ | m.p. 86–87° | calc. found | 71.63 71.58 | 6.68 6.67 | 4.64% 4.62% | |
| 104 | H | 4-Bromobenzyl | Methyl | —N(CH₃)₂ | m.p. 101–102° | calc. found | 62.43 62.35 | 5.82 5.86 | 4.04% 3.96% | |
| 105 | H | 2-Chlorobenzyl | Methyl | —N(CH₃)₂ | oil | calc. found | 71.63 71.12 | 6.68 6.66 | 4.64% 4.35% | |
| 106 | H | 3,4-Dimethoxybenzyl | Methyl | —N(CH₃)₂ | m.p. 116–117° | calc. found | 73.36 73.03 | 7.69 7.69 | 4.27% 4.11% | |
| 107 | H | 4-Methylbenzyl | Methyl | —N(CH₃)₂ | oil | calc. found | 81.10 80.57 | 8.24 8.23 | 4.98% 4.94% | |
| 108 | H | 4-Methylthiobenzyl | Methyl | —N(CH₃)₂ | oil | calc. found | 72.80 72.70 | 7.40 7.39 | 4.47% 4.34% | |
| 109 | H | 4-Fluorobenzyl | Methyl | —N(CH₃)₂ | oil | calc. found | 75.76 75.82 | 7.06 7.09 | 4.91% 4.74% | |
| 110 | H | 4-Methoxybenzyl | Methyl | —N(CH₃)₂ | oil | calc. found | 76.74 76.39 | 7.80 7.78 | 4.70% 4.51% | |
| 111 | F | Methallyl | Ethyl | —N(morpholino) | oil | | | | | |
| 112 | F | 2-Butenyl | Ethyl | —N(morpholino) | oil | | | | | |
| 113 | N-morpholino | Allyl | Ethyl | —N(CH₃)(Benzyl) | oil | calc. found | 76.49 76.58 | 8.22 8.30 | 7.14% 6.81% | |
| 114 | N-morpholino | Allyl | Ethyl | —N(CH₃)(Allyl) | oil | calc. found | 73.65 73.68 | 8.83 8.82 | 8.18% 7.90% | |

TABLE 1-continued

[Structure: R⁵-C₆H₄-C(R¹)(R²)-CO-NR³R⁴]

| Compound No. | R⁵ | R¹ | R² | —NR³R⁴ | Physical properties | | Analysis C | H | N | S |
|---|---|---|---|---|---|---|---|---|---|---|
| 115 | morpholino | Benzyl | Ethyl | —N(CH₃)(Benzyl) | m.p. 60-65° | calc.<br>found | 78.70<br>78.59 | 7.74<br>7.87 | 6.33%<br>6.66% | |
| 116 | morpholino | Benzyl | Ethyl | —N(CH₃)(C₄H₉) | oil | calc.<br>found | 76.43<br>76.31 | 8.88<br>8.83 | 6.86%<br>6.73% | |
| 117 | morpholino | Allyl | Ethyl | —N(CH₃)(C₄H₉) | oil | calc.<br>found | 73.70<br>73.60 | 9.56<br>9.56 | 7.81%<br>7.66% | |
| 118<br>119 | CH₃CONH— | Benzyl<br>Benzyl | Ethyl<br>Propyl | —N(CH₃)₂<br>—N(CH₃)₂ | glass<br>glass | calc.<br>found | 75.75<br>76.08 | 8.48<br>8.54 | 7.36%<br>6.96% | |
| 120 | morpholino | Allyl | Propyl | —N(CH₃)₂ | m.p. 62-64° | calc.<br>found | 72.69<br>72.51 | 9.15<br>8.97 | 8.48%<br>8.53% | |
| 121 | CH₃OCH₂CH₂O— | Allyl | Methyl | morpholino | oil | calc.<br>found | 68.44<br>68.26 | 8.16<br>8.24 | 4.20%<br>3.97% | |
| 122 | HOCH₂CH₂S— | Allyl | Isopropyl | morpholino | oil | | | | | |
| 123 | Br | Allyl | Methyl | morpholino | oil | | | | | |

TABLE 1-continued

Structure:

$R^5$–C$_6$H$_4$–CO–C($R^1$)($R^2$)–CO–NR$^3$R$^4$

| Compound No. | R$^5$ | R$^1$ | R$^2$ | —NR$^3$R$^4$ | Physical properties | | Analysis C | H | N | S |
|---|---|---|---|---|---|---|---|---|---|---|
| 124 | Br | Allyl | Isopropyl | | oil | calc. found | 64.45 64.78 | 7.51 7.48 | 4.18 3.92 | 9.56% 9.63% |
| 125 | HOCH$_2$CH$_2$S— | Allyl | Methyl | morpholino (—N⌒O) | oil | calc. found | 70.75 70.75 | 8.37 8.25 | 3.75% 3.76% | |
| 126 | CH$_2$=CHCH$_2$OCH$_2$CH$_2$O— | Allyl | Ethyl | morpholino | oil | | | | | |
| 127 | CH$_2$=CHCH$_2$OCH$_2$CH$_2$O— | Allyl | Methyl | morpholino | oil | | | | | |
| 128 | CH$_3$OCH$_2$CH$_2$O— | Allyl | Ethyl | morpholino | oil | calc. found | 69.14 69.23 | 8.41 8.34 | 4.03 3.93% | |
| 129 | CH$_3$OCH$_2$CH$_2$NH— | Benzyl | Ethyl | —N(CH$_3$)$_2$ | oil | | | | | |
| 130 | CH$_3$NH— | Benzyl | Ethyl | —N(CH$_3$)$_2$ | oil | | | | | |
| 131 | CH$_3$CON(CH$_3$)— | Benzyl | Ethyl | —N(CH$_3$)$_2$ | oil | | | | | |
| 132 | morpholino-linked (—N⌒O) | Benzyl | Ethyl | —N(C$_2$H$_5$)$_2$ | m.p. 76–79° | calc. found | 76.10 75.83 | 8.69 8.64 | 7.10% 7.09% | |
| 133 | morpholino-linked (—N⌒O) | Allyl | Ethyl | —N(C$_2$H$_5$)$_2$ | oil | calc. found | 73.22 73.03 | 9.36 9.40 | 8.13% 7.64% | |

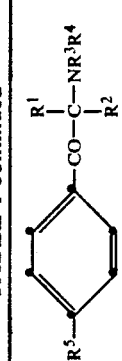

TABLE 1-continued
| Compound No. | $R^5$ | $R^1$ | $R^2$ | $-NR^3R^4$ | Physical properties | | Analysis | | |
|---|---|---|---|---|---|---|---|---|---|
| | | | | | | | C | H | N | S |
| 270 | [morpholino] | Allyl | Ethyl | —N(CH$_2$CH$_2$OCH$_3$)$_2$ | oil | calc.<br>found | 68.29<br>67.91 | 8.97<br>9.21 | 6.92%<br>6.75% | |

TABLE 2

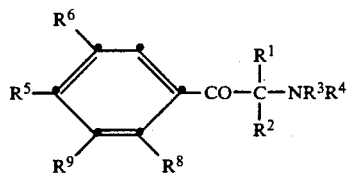

| Compound No. | R⁵ | R⁶ | R⁸ | R⁹ | R¹ | R² | —NR³R⁴ | Physical properties | | Analysis C | H | N |
|---|---|---|---|---|---|---|---|---|---|---|---|---|
| 140 | $CH_3O-$ | $CH_3$ | H | $CH_3$ | Benzyl | Ethyl | $-N(CH_3)_2$ | m.p. 68–70° | calc. | 77.84 | 8.61 | 4.13% |
| | | | | | | | | | found | 77.71 | 8.63 | 3.93% |
| 141 | Cl | H | Cl | H | Benzyl | Ethyl | $-N(CH_3)_2$ | oil | calc. | 65.15 | 6.04 | 4.00% |
| | | | | | | | | | found | 65.07 | 5.93 | 3.95% |
| 142 | Cl | Cl | H | H | Allyl | Ethyl | $-N(CH_3)_2$ | oil | calc. | 60.01 | 6.38 | 4.67% |
| | | | | | | | | | found | 59.95 | 6.39 | 4.80% |
| 143 | Cl | Cl | H | H | Benzyl | Ethyl | $-N(CH_3)_2$ | oil | calc. | 65.15 | 6.04 | 4.00% |
| | | | | | | | | | found | 65.19 | 6.23 | 3.86% |
| 144 | morpholino | Cl | H | H | Allyl | Ethyl | $-N(CH_3)_2$ | oil | calc. | 65.04 | 7.76 | 7.98% |
| | | | | | | | | | found | 64.40 | 7.82 | 7.72% |
| 145 | morpholino | Cl | H | H | Benzyl | Ethyl | $-N(CH_3)_2$ | m.p. 110–111° | | | | |
| 146 | $(CH_3)_2N-$ | H | H | $C_2H_5$ | Benzyl | Ethyl | $-N(CH_3)_2$ | oil | | | | |
| 147 | $(CH_3)_2N-$ | H | $CH_3$ | H | Benzyl | Ethyl | $-N(CH_3)_2$ | m.p. 101–103° | calc. | 78.06 | 8.93 | 8.28% |
| | | | | | | | | | found | 77.97 | 8.92 | 8.22% |

TABLE 3

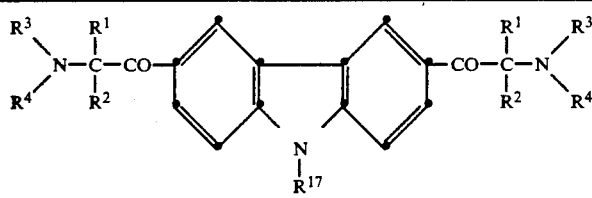

| Compound No. | R¹ | R² | —NR³R⁴ | R¹⁷ | Physical property | | C | H | N |
|---|---|---|---|---|---|---|---|---|---|
| 148 | Benzyl | Ethyl | $-N(CH_3)_2$ | $C_4H_9$ | glass | calc. | 80.08 | 8.16 | 6.67% |
| | | | | | | found | 80.24 | 7.40 | 6.41% |
| 149 | Allyl | Methyl | morpholino | $C_4H_9$ | glass | calc. | 73.81 | 8.09 | 7.17% |
| | | | | | | found | 73.66 | 8.05 | 6.87% |

TABLE 4

Salts

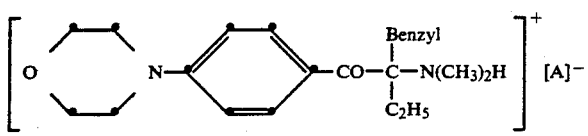

| Compound No. | A | Melting point | | Analysis C | H | N |
|---|---|---|---|---|---|---|
| 150 | $CF_3COO-$ | 55–56° | calc. | 62.49 | 6.50 | 5.83% |
| | | | found | 62.18 | 6.64 | 5.54% |

TABLE 4-continued

Salts $$\left[ \underset{O}{\bigcirc}N-\underset{}{\bigcirc}-CO-\underset{\underset{C_2H_5}{|}}{\overset{\overset{Benzyl}{|}}{C}}-N(CH_3)_2H \right]^+ [A]^-$$

| Compound No. | A | Melting point | Analysis |  |  |  |
|---|---|---|---|---|---|---|
| | | | | C | H | N |
| 151 | CH₃—⬡—SO₃⁻ | 90–95° | calc. | 66.89 | 7.11 | 5.20% |
| | | | found | 66.76 | 7.38 | 4.78% |
| 152 | CH₂SO₃⁻ on cyclohexanone with CH₃—C—CH₃ | 95–105° | calc. | 66.19 | 7.74 | 4.68% |
| | | | found | 65.57 | 8.04 | 4.38% |

EXAMPLE 5

Photocuring of a blue printing ink

A blue printing ink is prepared in accordance with the following formulation:
62 parts of Setalin ® AP 565 (urethane acrylate resin from Synthese, Holland),
15 parts of 4,4'-di-(β-acryloyloxyethoxy)-2,2-diphenyl-propane (Ebecryl ® 150, UCB, Belgium) and
23 parts of Irgalithblau ® GLSM (Ciba-Geigy AG, Basle).

The mixture is homogenized on a 3-roll mill and ground down to a particle size of <5 μm.

In each case 5 g of this printing ink are mixed homogeneously with the desired amount of photoinitiator on a plate grinding machine under a pressure of 180 kg/m², while cooling with water. Samples with 3% and 6% of photoinitiator—based on the printing ink—are prepared.

Offset prints are made from these printing inks on 4×20 cm strips of art printing paper using a specimen printing apparatus (Prüfbau, FR Germany). The printing conditions are: amount of printing ink applied: 1.5 g/m², pressing pressure (line pressure): 25 kp/cm, printing speed: 1 m/second.

A printing roller with a metallic surface(aluminium) is used here.

The printed samples are cured in a UV irradiation apparatus from PPG using two lamps of 80 W/cm each. The irradiation time is varied by varying the rate of transportation of the sample.

The surface drying of the printing ink is tested by the so-called transfer test immediately after the irradiation. White paper is thereby pressed onto the printed sample under a line pressure of 25 kp/cm. If the paper remains colourless, the test has been passed. If visible amounts of colour are transferred to the test strips, this is an indication that the surface of the sample has not cured sufficiently.

The maximum rate of transportation at which the transfer test was still passed is shown in Table 5.

To test for complete curing of the printing ink, offset prints are likewise produced as described above, but printing rollers with a rubber surface are used and the metallic side of aluminum-coated strips of paper are printed.

The irradiation is carried out as described above. Complete curing is tested in a REL complete curing tester immediately after the irradiation. In this, an aluminium cylinder over which fabric is stretched is placed on the printed sample and rotated once around its own axis under a pressure of 220 g/cm² in the course of 10 seconds. If visible damage is thereby caused to the sample, the printing ink has not completely cured sufficiently. The maximum rate of transportation at which the REL test was still passed is given in the tables.

TABLE 5

| Photoinitiator | Concentration | Transfer Test (m/min) | REL Test (m/min) |
|---|---|---|---|
| Compound No. 1 | 3% | >170 | 150 |
| | 6% | >170 | >170 |
| Compound No. 2 | 3% | >170 | 130 |
| | 6% | >170 | >170 |
| Compound No. 3 | 3% | >170 | 140 |
| | 6% | >170 | >170 |
| Compound No. 4 | 3% | >170 | 130 |
| | 6% | >170 | >170 |
| Compound No. 5 | 3% | >170 | 120 |
| | 6% | >170 | >170 |
| Compound No. 6 | 3% | >170 | 160 |
| | 6% | >170 | >170 |
| Compound No. 7 | 3% | >170 | 130 |
| | 6% | >170 | >170 |
| Compound No. 8 | 3% | >170 | 150 |
| | 6% | >170 | >170 |
| Compound No. 9 | 3% | >170 | 130 |
| | 6% | >170 | >170 |
| Compound No. 10 | 3% | >170 | 130 |
| | 6% | >170 | 160 |

TABLE 5-continued

| Photoinitiator | Concentration | Transfer Test (m/min) | REL Test (m/min) |
|---|---|---|---|
| Compound No. 11 | 3% | >170 | 130 |
|  | 6% | >170 | 160 |
| Compound No. 39 | 3% | 140 | 80 |
|  | 6% | >170 | 140 |
| Compound No. 40 | 3% | 110 | 70 |
|  | 6% | 140 | 70 |
| Compound No. 41 | 3% | >170 | 110 |
|  | 6% | >170 | 150 |
| Compound No. 42 | 3% | 110 | 60 |
|  | 6% | >170 | 90 |
| Compound No. 44 | 3% | 110 | 70 |
|  | 6% | >170 | 110 |
| Compound No. 45 | 3% | >170 | 110 |
|  | 6% | >170 | 160 |
| Compound No. 46 | 3% | >170 | 120 |
|  | 6% | >170 | 160 |
| Compound No. 47 | 3% | >170 | 50 |
| Compound No. 48 | 3% | >170 | 110 |
| Compound No. 51 | 3% | 70 | 50 |
|  | 6% | >170 | 110 |
| Compound No. 53 | 3% | 120 | 60 |
|  | 6% | >170 | 130 |
| Compound No. 63 | 3% | 80 | 40 |
|  | 6% | >170 | 80 |
| Compound No. 91 | 3% | 110 | 70 |
|  | 6% | >170 | 70 |
| Compound No. 92 | 3% | >170 | 100 |
|  | 6% | >170 | 120 |
| Compound No. 118 | 3% | 140 | 100 |
| Compound No. 119 | 3% | 160 | 80 |
| Compound No. 120 | 3% | 170 | 150 |
| Compound No. 121 | 3% | 120 | 90 |
| Compound No. 125 | 3% | 130 | 100 |
| Compound No. 148 | 3% | 120 | 80 |
| Compound No. 149 | 3% | 170 | 110 |

EXAMPLE 6

Photocuring of a white lacquer

A white lacquer is prepared in accordance with the following formulation:
17.6 g of Ebecryl ® 593 (polyester acrylate resin from UCB, Belgium),
11.8 g of N-vinylpyrrolidone,
19.6 g of titanium dioxide RTC-2 (titanium dioxide from Tioxide, England),
19.6 g of Sachtolith ® HDS (lithopone from Sachtleben Chemie, FRG),
11.8 g of trimethylolpropane trisacrylate and
19.6 g of Setalux ® UV 2276 (acrylated epoxy resin based on bisphenol A, Kunstharzfabrik Synthese, Holland).

The above components are ground down to a particle size of not more than 5 μm together with 125 g of glass beads (diameter 4 mm) in a 250 ml glass bottle for at least 24 hours.

The stock paste thus obtained is divided into portions, each portion is mixed with in each case 2% of the photoinitiators shown in Table 6 by stirring at 60° C. and the mixtures are ground again with glass beads for 16 hours.

The white lacquers thus prepared are applied in a thickness of 70 μm to glass plates using a doctor blade. The samples are exposed on the one hand in a PPG irradiation apparatus with a 80 W/cm lamp and on the other hand in an irradiation apparatus from Fusion Systems (USA) using a D lamp, in each case in one passage. The rate of passage of the samples through the irradiation apparatus is thereby increased continuously until adequate curing no longer occurs. The maximum rate at which a lacquer film which is still wipe-proof forms is shown in Table 6 as "curing rate".

TABLE 6

| Photoinitiator | Curing rate (m/minute) | |
|---|---|---|
| (in each case 2%) | PPG apparatus 80 W | Fusion D lamp |
| Compound No. 1 | 60 | 130 |
| Compound No. 3 | 50 | 170 |
| Compound No. 4 | 50 | 110 |
| Compound No. 6 | 140 | >200 |
| Compound No. 7 | 80 | >200 |
| Compound No. 8 | 70 | 150 |
| Compound No. 12 | 50 | 120 |
| Compound No. 14 | 70 | — |
| Compound No. 15 | 50 | — |

EXAMPLE 7

Sensitized photocuring of a white lacquer

The procedure is as in Example 6. However, in addition to the 2% of photoinitiator, 0.5% (based on the lacquer) of isopropylthioxanthone is also added as a sensitizer. A noticeable increase in the curing rate thereby occurs. The results are shown in Table 7.

TABLE 7

| Photoinitiator | | Curing rate (m/minute) | |
|---|---|---|---|
| (in each case 2%) | Sensitizer | PPG apparatus | Fusion D lamp |
| Compound No. 1 | — | 60 | 130 |
|  | 0.5% | 130 | 180 |
| Compound No. 3 | — | 50 | 170 |
|  | 0.5% | 100 | >200 |
| Compound No. 4 | — | 50 | 110 |
|  | 0.5% | 80 | 160 |
| Compound No. 6 | — | 140 | >200 |
|  | 0.5% | 170 | >200 |
| Compound No. 7 | — | 80 | >200 |
|  | 0.5% | 170 | >200 |
| Compound No. 8 | — | 70 | 150 |
|  | 0.5% | 120 | >200 |
| Compound No. 12 | — | 50 | 120 |
|  | 0.5% | 110 | >200 |

EXAMPLE 8

Photocuring of a black offset printing ink

A photocurable black offset printing ink is mixed with in each case 3% of the photoinitiators shown in Table 8 and paper laminated with aluminium foil is printed with the ink in an application amount of 1.5 g/m², the procedure being as in Example 5. Curing is also carried out as described in Example 5 in the PPG apparatus with two lamps of 80 Watt. The curing is checked byt eh transfer test—as described in Example 5. Table 8 indicates the maximum rate of transportation in the irradiation apparatus at which the transfer test is still just passed.

TABLE 8

| Photoinitiator | Curing rate PPG apparatus (m/min) |
|---|---|
| Compound No. 6 | 120 |
| Compound No. 8 | 130 |
| Compound No. 9 | 130 |
| Compound No. 10 | 110 |

EXAMPLE 9

Preparation of a photoresist

A mixture of

| | |
|---|---|
| 37.64 g | pentaerythritol trisacrylate |
| 10.76 g | hexamethoxymethylmelamine (Cymel ® 301, Cyanamid Corp.) |
| 47.30 g | of a thermoplastic carboxylated polyacrylate (Carboset ® 525, Goodrich Corp.) and |
| 4.30 g | of polyvinylpyrrolidone |
| 100.00 g | | is dissolved in a mixture of 319 g methylene chloride and 30 g methanol. To this solution are added 0.5 g Irgalithgreen ® GLN (Ciba-Geigy AG) and compound 10 as photoinitiator in the amounts indicated in table 9.

The viscous solution is applied to aluminium sheets in a thickness of 200 μm. After drying for 15 minutes at 60° the thickness is about 45 μm. The sample is covered with a polyester sheet (76 μm). An optical 21 step wedge (Stouffer wedge) is placed on the sheet and fixed by vacuum. The sample is irradiated for 20 seconds through the wedge with a 5 kW lamp at a distance of 30 cm. Afterwards the sheet is removed and the sample is developed in an ultrasonics bath. The developer employed is a solution of 15 g of $Na_2SiO_3 \cdot 9H_2O$, 0.16 g of KOH, 3 g of polyethylene glycol 6000 and 0.5 g of levulinic acid in 1000 g of water. After being briefly dried at room temperature, the samples are assessed. Table 9 indicates the highest step which is completely reproduced and has a non tacky surface. The higher the step, the more sensitive is the system.

TABLE 9

| Initiator | Highest step |
|---|---|
| 0.1% of compound No. 10 | 10 |
| 0.5% of compound No. 10 | 14 |
| 1.0% of compound No. 10 | 16 |

EXAMPLE 10

Preparation of a printing plate 88.6 parts of a butadiene/styrene copolymer (Cariflex ® TR 1107, Shell Chemie) are plastisized on a calander at 140°. Then 11 parts of hexanediol diacrylate, 0.3 part of a phenolic antioxidant (Topano ® OC, ICI Comp.), 0.01 part of Sudan Black B and 0.4 part of compound 10 are admixed at 100° and the mixture is homogenized at this temperature.

Plates of 2 mm thickness are pressed from this mixture between two polyester sheets. The back of the plates is irradiated through the sheet in a BASF-Nyloprint irradiation device with 40 W lamps. The sheet on the face of the plate is replaced by a test negative and this side is exposed for 6 minutes through this negative.

The exposed sample is developed in a brushing bath with a mixture of 4 parts of tetrachloroethylene and 1 part of butanol, while washing out the soluble parts. After drying for 60 minutes at 80° the second sheet is removed and the printing plate is immersed successively in a 0.4 % aqueous bromine solution and a 1.5 % solution of $Na_2S_2O_3/Na_2CO_3$ followed by rinsing with water.

Finally, each side is irradiated for a further 6 minutes. All parts of the test negative are reproduced clearly. The depth of the indentations is 34 μm, the hight of the relief is 450 μm.

What is claimed is:

1. A compound of the formula I

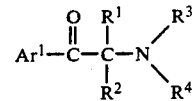

in which
$Ar^1$ is an aromatic radical of the formula IV

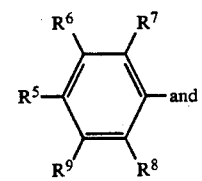

$R^1$ is either (a) a radical of the formula

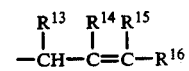

or (b) a radical of the formula $-CH(R^{13})-Ar^2$, in which $Ar^2$ is a phenyl radical which is unsubstituted or substituted by halogen, $C_1$-$C_{12}$alkyl, $C_1$-$C_4$alkoxy, or $-(OCH_2CH_2)_nOCH_3$, n being 1-10,
$R^2$ has one of the meanings for $R^1$ or is $C_1$-$C_8$alkyl,
$R^3$ and $R^4$ independently of one another are $C_1$-$C_{12}$alkyl, $C_2$-$C_4$alkyl which is substituted by $C_1$-$C_4$alkoxy, $-CN$ or $-COO(C_1$-$C_4$alkyl), allyl, cyclohexyl or benzyl, or $R^3$ and $R^4$ together are $C_4$-$C_6$alkylene, which can be interrupted by $-O-$ or $-N(R^{17})-$,
$R^5$ is a group $-N(R^{30})(R^{21})$
$R^6$ is hydrogen, halogen, $C_1$-$C_4$alkyl or one of the meanings of $R^5$,
$R^7$ and $R^8$ are hydrogen or halogen,
$R^9$ is hydrogen or $C_1$-$C_4$alkyl,
$R^{11}$ is hydrogen, $C_1$-$C_4$alkyl, allyl, benzyl or $C_2$-$C_4$alkanoyl,
$R^{13}$, $R^{14}$, $R^{15}$ and $R^{16}$ independently of one another are hydrogen or methyl,
$R^{17}$ is hydrogen, $C_1$-$C_4$alkyl, benzyl, 2-hydroxyethyl or acetyl, and
$R^{20}$ and $R^{21}$ independently of one another are hydrogen, $C_1$-$C_{12}$alkyl, $C_2$-$C_6$alkoxyalkyl, acetyl, allyl or benzyl, or $R^{20}$ and $R^{21}$ together are $C_4$-$C_6$alkylene, which can be interrupted by $-O-$ or $-N(R^{17})-$.

2. A compound according to claim 1, in which $Ar^1$ is a group of the formula IV in which $R^5$ is a group $-N(R^{20})(R^{21})$, $R^6$ is hydrogen, chlorine or $C_1$-$C_4$alkyl or has one of the meanings given for $R^5$, $R^7$ and $R^8$ are hydrogen or chlorine, $R^9$ is hydrogen or $C_1$-$C_4$alkyl, $R^1$ is either (a) a radical of the formula $-CH_2-C(R^{14})=CH(R^{15})$ or (b) a radical of the formula $-CH_2-Ar^2$, in which $Ar^2$ is a phenyl radical which is unsubstituted or substituted by halogen, $C_1$-$C_{12}$alkyl, $C_1$-$C_4$-alkoxy, $-(OCH_2CH_2)_nOCH_3$ or benzoyl, n being 1-10, $R^2$ has one of the meanings given for $R^1$ or is $C_1$-$C_8$alkyl, $R^3$ and $R^4$ independently of one another are $C_1$-$C_6$alkyl, 2-methoxyethyl, allyl or benzyl, or $R^3$ and $R^4$ together are tetramethylene, pentamethylene or 3-oxapentamethylene, $R^{14}$ and $R^{15}$ are hydrogen or methyl, and $R^{20}$ and $R^{21}$ are hydrogen, $C_1$-$C_4$-alkyl, 2-methoxyethyl, acetyl or allyl, or $R^{20}$ and $R^{21}$ together are $C_4$-$C_5$alkylene, which can be interrupted by —O— or —N($CH_3$)—.

3. A compound according to claim 2 in which $R^5$ is a group, $R^7$ and $R^8$ are hydrogen, $R^1$ is a radical of the formula

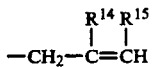

and all the other substituents are as defined in claim 2.

4. A compound according to claim 3, in which $R^6$ and $R^9$ are hydrogen and all the other substituents are as defined in claim 3.

5. A compound according to claim 3 in which $R^1$ is allyl and all the other substituents are as defined in claim 3.

6. A compound according to claim 2 in which $R^5$ is a group —N($R^{20}$)($R^{21}$), $R^7$ and $R^8$ are hydrogen and all the other substituents are as defined in claim 2.

7. A compound according to claim 6, in which $R^6$ and $R^9$ are hydrogen and all the other substituents are as defined in claim 6.

8. A compound according to claim 6, in which $R^1$ is allyl or benzyl and all the other substituents are as defined in claim 6.

* * * * *

UNITED STATES PATENT AND TRADEMARK OFFICE
CERTIFICATE OF CORRECTION

PATENT NO. : 5,077,402
DATED : Dec. 31, 1991
INVENTOR(S) : Desobry et al.

It is certified that error appears in the above-identified patent and that said Letters Patent is hereby corrected as shown below:

COLUMN 58
Claim 1: line 37 should read: --$R^5$ is a group $N(R^{20})(R^{21})$.--

Signed and Sealed this

First Day of October, 1996

Attest:

BRUCE LEHMAN

Attesting Officer

Commissioner of Patents and Trademarks